United States Patent
Shpall et al.

(10) Patent No.: US 11,766,402 B2
(45) Date of Patent: Sep. 26, 2023

(54) METHODS FOR PRODUCTION OF MSC-DERIVED EXOSOMES

(71) Applicant: Board of Regents, The University of Texas System, Austin, TX (US)

(72) Inventors: Elizabeth Shpall, Houston, TX (US); Raghu Kalluri, Houston, TX (US); Katy Rezvani, Houston, TX (US); Mayela Mendt, Houston, TX (US); Valerie Lebleu, Houston, TX (US); Sushrut Kamerkar, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 519 days.

(21) Appl. No.: 16/762,439

(22) PCT Filed: Nov. 16, 2018

(86) PCT No.: PCT/US2018/061657
§ 371 (c)(1),
(2) Date: May 7, 2020

(87) PCT Pub. No.: WO2019/099927
PCT Pub. Date: May 23, 2019

(65) Prior Publication Data
US 2021/0186877 A1    Jun. 24, 2021

Related U.S. Application Data

(60) Provisional application No. 62/587,408, filed on Nov. 16, 2017.

(51) Int. Cl.
| | |
|---|---|
| A61K 35/28 | (2015.01) |
| C12N 15/113 | (2010.01) |
| A61K 9/127 | (2006.01) |
| A61K 9/00 | (2006.01) |
| A61K 31/7105 | (2006.01) |
| A61K 31/713 | (2006.01) |
| A61K 45/06 | (2006.01) |
| C12N 5/0775 | (2010.01) |
| C12Q 1/68 | (2018.01) |

(52) U.S. Cl.
CPC .......... *A61K 9/1271* (2013.01); *A61K 9/0019* (2013.01); *A61K 31/713* (2013.01); *A61K 31/7105* (2013.01); *A61K 35/28* (2013.01); *A61K 45/06* (2013.01); *C12N 5/0663* (2013.01); *C12N 5/0667* (2013.01); *C12N 15/1137* (2013.01); *C12N 2310/14* (2013.01); *C12N 2310/141* (2013.01); *C12N 2320/31* (2013.01); *C12N 2320/32* (2013.01); *C12N 2500/02* (2013.01); *C12N 2500/90* (2013.01)

(58) Field of Classification Search
None
See application file for complete search history.

(56) References Cited

U.S. PATENT DOCUMENTS

| | | |
|---|---|---|
| 2014/0220053 A1 | 8/2014 | Muraca et al. |
| 2015/0190429 A1 | 7/2015 | Beelen et al. |
| 2017/0119682 A1 | 5/2017 | De La Rosa et al. |
| 2017/0121685 A1 | 5/2017 | De La Rosa et al. |
| 2017/0183686 A1* | 6/2017 | Khvorova .......... C12N 15/1137 |

FOREIGN PATENT DOCUMENTS

| | | |
|---|---|---|
| JP | 2012-524052 | 10/2012 |
| WO | WO 2010/119256 | 10/2010 |
| WO | 2011/000551 A1 | 1/2011 |
| WO | 2012/087241 A1 | 6/2012 |
| WO | 2013/172793 A1 | 11/2013 |
| WO | 2017/023689 A1 | 2/2017 |

OTHER PUBLICATIONS

Baglio et al: "Human bone marrow- and adipose-mesenchymal stem cells secrete exosomes enriched in distinctive niRNA and tRNA species", Stem Cell Research & Therapy, vol. 6, No. 127, Jul. 1, 2015 (Jul. 1, 2015), pp. 1-20.
Blazquez et al: "Immunomodulatory Potential of Human Adipose Mesenchymal Stem Cells Derived Exosomes on in vitro Stimulated T Cells", Frontiers in Immunology, vol. 5, Oct. 4, 2014 (Oct. 4, 2014), pp. 1-9.
English translation of Office Communication issued in Japanese Patent Application No. 2020-527090, dated Aug. 23, 2022.
Pachler et al., "A Good Manufacturing Practice-grade standard protocol for exclusively human mesenchymal stromal cell-derived extracellular vesicles," Cytotherapy, 19(4):458-472, 2017.
Watson et al., "Efficient production and enhanced tumor delivery of engineered extracellular vesicles," Biomaterials, 105:195-205, 2016.

* cited by examiner

*Primary Examiner* — Sean McGarry
(74) *Attorney, Agent, or Firm* — Norton Rose Fulbright US LLP

(57) ABSTRACT

Provided herein are methods of manufacturing clinical grade exosomes derived from mesenchymal stem cells (MSCs). Further provided are methods of loading the exosomes with therapeutic agents, such as siRNA. Also provided herein are methods of treating diseases by administering the clinical grade exosomes.

37 Claims, 31 Drawing Sheets

| | Step 1 | Step 2 | Step 3 | Step 4 | Step 5 | Step 6 |
|---|---|---|---|---|---|---|
| IC Inlet | | | Reagent | Wash | None | IC Media |
| IC Inlet Rate | | | 10 | 10 | 0 | 100 |
| IC Circ. Rate | Load Cell Expansion set | Prime Cell Expansion set | 100 | 100 | 20 | -17 |
| EC Inlet | | | None | None | Wash | IC Media |
| EC Inlet Rate | | | 0 | 0 | 0.1 | 148 |
| EC Circ. Rate | | | 30 | 30 | 30 | -1.7 |
| Outlet | | | EC Outlet | EC Outlet | EC Outlet | IC & EC Outlet |
| Rocker Control | | | Stationary (0) | Stationary (0) | Stationary (0) | In Motion (-90, 180, 1) |
| Stop Condition | | | Empty Bag | IC Volume (22mL) | Manual | Exchange (2.5 IC, 2.5 EC) |
| Time | 10 min | 35 min | 10 min | 2 min | Overnight | 5 min |
| Necessary Volume | | 2L PBS | 100mL | 22mL | 100mL | 500mL 800mL |

Step 3–Step 5: *Coat Bioreactor*
Step 6: *IC EC Washout*

Between Step 2 and Step 3: *Remove IC Air / Remove EC Air*
After Step 6: *Inlet Line Washout*

| | Complete media | | Load Cells | | | Attach Cells |
|---|---|---|---|---|---|---|
| | Step 7 | Step 8 | Step 9 | Step 10 | Step 11 | Step 12 |
| | None | None | Cell | IC Media | None | None |
| | 0 | 0 | 25 | 25 | 10 | 0 |
| | 100 | 100 | 150 | 150 | 200 | 0 |
| | IC Media | IC Media | None | None | None | IC Media |
| | 0.1 | 0.1 | 0 | 0 | 0 | 0.1 |
| | 250 | 30 | 30 | 30 | 30 | 30 |
| | EC Outlet | EC Outlet | EC Outlet | EC Outlet | EC Outlet | EC Outlet |
| | Stationary (0) | Stationary (0) | In Motion (-90,180,1) | In Motion (-90,180,1) | In Motion (-90,180,1) | Stationary (180) |
| | Time (10 min) | Manual | Empty Bag | IC Volume (47mL) | Time (2 min) | Manual |
| | 10 min | 50-230min | 4 min | 2 min | 2 min | 1440 min |
| | 1mL | <24mL | 100mL | 47mL | 0mL | 144mL |

Remove IC Air
Remove EC Air

Inlet Line Washout

FIG. 1A
(Cont'd)

MSC-conditioned media (exosomes) collection (6x48 hr shown)

| | Step 19<br>Feeding<br>(48hrs) | Step 20<br>Harvest<br>1 | Step 21<br>Feeding<br>(48hrs) | Step 22<br>Harvest<br>2 | Step 23<br>Feeding<br>(48hrs) | Step 24<br>Harvest<br>3 |
|---|---|---|---|---|---|---|
| IC Inlet | None | EC media | None | EC media | None | EC media |
| IC Inlet Rate | 0ml/min | 25ml/min | 0ml/min | 20ml/min | 0ml/min | 15ml/min |
| IC Circ. Rate | 5ml/min | 5ml/min | 5ml/min | 5ml/min | 5ml/min | 5ml/min |
| EC Inlet | EC media | None | EC media | None | EC media | None |
| EC Inlet Rate | 0.8ml/min | 0ml/min | 0.7ml/min | 0ml/min | 0.6ml/min | 0ml/min |
| EC Circ. Rate | 30ml/min | 30ml/min | 30ml/min | 30ml/min | 30ml/min | 30ml/min |
| Outlet | EC Outlet | Harvest | EC Outlet | Harvest | EC Outlet | Harvest |
| Rocker | Stationary at 0 | Stationary at 0 | Stationary at 0 | Stationary at 0 | Stationary at 0 | Stationary at 0 |
| Stop Condition | Time (2880min) | Time (10min) | Time (2880min) | Time (13min) | Time (2880min) | Time (17min) |
| Time | 2880min | 10min | 2880min | 13min | 2880min | 17min |
| Necessary Volume | 2304ml | 250ml | 2016ml | 250ml | 1728ml | 250ml |

Remove IC Air
Remove EC Air

*FIG. 1A*
*(Cont'd)*

MSC-conditioned media (exosomes) collection (6x48 hr shown)

| Step 25 | Step 26 | Step 27 | Step 28 | Step 29 | Step 30 |
|---|---|---|---|---|---|
| Feeding (48hrs) | Harvest 4 | Feeding (48hrs) | Harvest 5 | Feeding (48hrs) | Harvest 6 |
| None | EC media | None | EC media | None | EC media |
| 0ml/min | 10ml/min | 0ml/min | 5ml/min | 0ml/min | 5ml/min |
| 5ml/min | 5ml/min | 5ml/min | 5ml/min | 5ml/min | 5ml/min |
| EC media | None | EC media | None | EC media | None |
| 0.5ml/min | 0ml/min | 0.4ml/min | 0ml/min | 0.4ml/min | 0ml/min |
| 30ml/min | 30ml/min | 30ml/min | 30ml/min | 30ml/min | 30ml/min |
| EC Outlet | Harvest | EC Outlet | Harvest | EC Outlet | Harvest |
| Stationary at 0 | Stationary at 0 | Stationary at 0 | Stationary at 0 | Stationary at 0 | Stationary at 0 |
| Time (2880min) | Time (25min) | Time (2880min) | Time (50min) | Time (2880min) | Time (50min) |
| 2880min | 25min | 2880min | 50min | 2880min | 50min |
| 1440ml | 250ml | 1152ml | 250ml | 1152ml | 250ml |

Remove IC Air
Remove EC Air

*FIG. 1A (Cont'd)*

| | Step 24* | Step 25* | Step 26* | Step 27* | Step 28* | Step 29* |
|---|---|---|---|---|---|---|
| | | Release of MSCs | | | Harvest | Upload Cell Expansion Set |
| | Wash | Reagent | Wash | None | IC Media | |
| | 100 | 50 | 50 | 0 | 400 | |
| | -17 | 300 | 300 | 300 | -70 | |
| | Wash | None | None | None | IC Media | |
| | 148 | 0 | 0 | 0 | 60 | |
| | -1.7 | 30 | 30 | 30 | 30 | |
| | IC & EC Outlet | EC Outlet | EC Outlet | EC Outlet | Harvest | |
| | In Motion (-90,180,1) | In Motion (-90,180,1) | In Motion (-90,180,1) | In Motion (-90,180,1) | In Motion (-90,180,1) | |
| | Exchange (2.5 IC, 2.5 EC) | Empty Bag | IC Volume (22ml) | Time (8min) | IC Volume (378ml) | |
| | 5min | 4min | 0.5min | 8min | 15min | 5min |
| | 1300ml | 200ml | 22ml | 0ml | 500ml 75ml | |

*Timeline for MSCs-derived exosomes production using a bioreactor*

| Day 0 | Day 1 | Day 2 | Day 3 | Day 4 | Day 5 | Day 6 | Day 7 | Day 8 | Day 9 |
|---|---|---|---|---|---|---|---|---|---|
| Preparation of bioreactor | Seeding of MSCs | \multicolumn{7}{c}{Expansion of MSCs in growth media} | | Wash with PBS and load PLT-free media |

| Day 11 | Day 13 | Day 15 | Day 17 | Day 19 | Day 21 |
|---|---|---|---|---|---|
| Bioreactor Harvest 1 → Freeze (-80°C) | Bioreactor Harvest 2 → Freeze (-80°C) | Bioreactor Harvest 3 → Freeze (-80°C) | Bioreactor Harvest 4 → Freeze (-80°C) | Bioreactor Harvest 5 → Freeze (-80°C) | Bioreactor Harvest 6 → Freeze (-80°C) |

*FIG. 1B*

|  | Harvest Time (days) | Volume (ml) | Protein (mg) | Exosomes ($\times 10^9$) |
|---|---|---|---|---|
| Harvest 1 | 10 | 250 | 2.641 | 2010 |
| Harvest 2 | 12 | 250 | 6.222 | 4493 |
| Harvest 3 | 14 | 250 | 3.606 | 3402 |
| Harvest 4 | 16 | 250 | 3.534 | 3100 |
| Harvest 5 | 18 | 250 | 0.992 | 983 |
| Harvest 6 | 20 | 250 | 1.040 | 1210 |
| Total |  | 1500 | 17.85 | 15,178 |

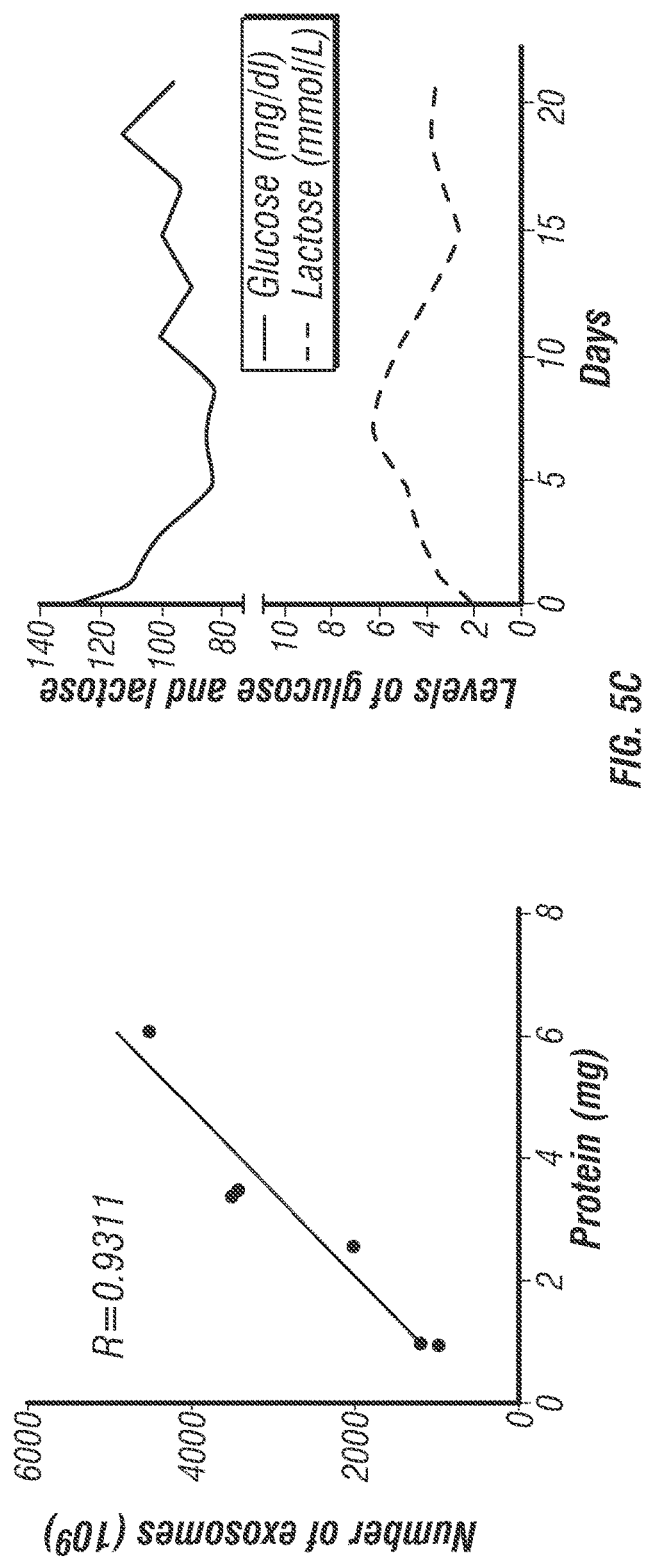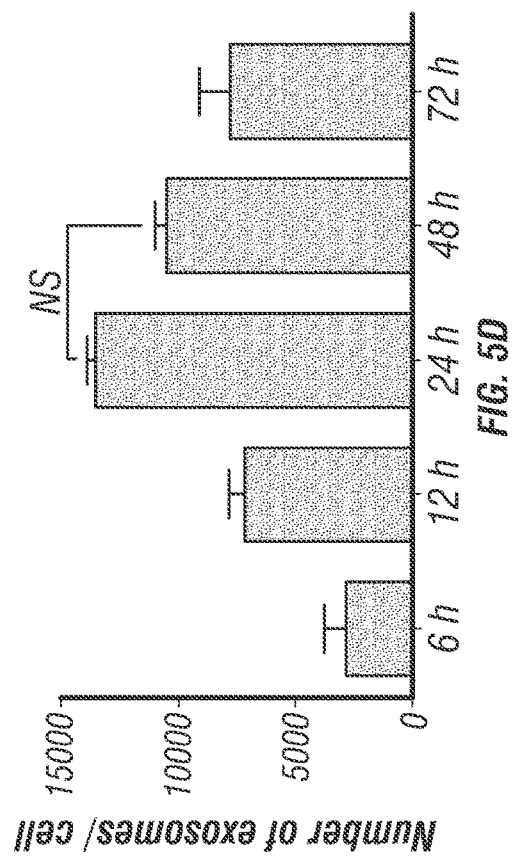
FIG. 5C
FIG. 5D

METHODS FOR PRODUCTION OF MSC-DERIVED EXOSOMES

This application is a national phase application under 35 U.S.C. § 371 that claims priority to International Application No. PCT/US2018/061657 filed Nov. 16, 2018, which claims the benefit of U.S. Provisional Application No. 62/587,408, filed Nov. 16, 2017, the entirety of which is incorporated herein by reference.

BACKGROUND

1. Field

The present invention relates generally to the fields of molecular biology and medicine. More particularly, it concerns methods for the large-scale production of good manufacturing practice—(GMP) compliant exosomes.

2. Description of Related Art

Extracellular vesicles (EVs), including exosomes and microvesicles, are nanosized intercellular communication vehicles that participate in several physiological processes. Specifically, exosomes are nano-sized vesicles released by cells and they constitute a mode of intercellular exchange of cellular components and products that has spurred a renewed interest in their utility as therapeutic delivery agents. Unlike their artificial counterparts, the features of these naturally-produced, specialized shuttle service between cells may offer unique advantages for the efficient delivery of therapeutic payloads. Such features of exosomes and regulatory machinery associated with exosomes production and cellular uptake remain to be further studied. Nonetheless, the use of exosomes for therapeutic control of diseases, including cancer, has already shown promising results.

Due to their biological properties, exosomes are promising candidates for the treatment of immune disorders and for the systemic delivery of therapeutic compounds, such as cytokines, chemotherapeutic drugs, nucleic acid and viral vectors. However, their low production yield limits their potential to be used in the clinic. Thus, there is an unmet need for efficient methods for producing exosomes that can be used for therapeutics.

SUMMARY

In a first embodiment, there is provided a method of manufacturing exosomes from mesenchymal stem cells (MSCs) comprising culturing the MSCs in a functionally closed bioreactor to confluency (e.g., 75-95% or 80-90% confluency, such as about 80%, 81%, 82%, 83%, 84%, 85%, 86%, 87%, 88%, 89%, or 90%) in media comprising human platelet lysate (PLT); further culturing the cells in media essentially free of PLT (e.g., free of PLT); collecting conditioned media fractions from the bioreactor; and isolating exosomes from the conditioned media fractions.

In some aspects, each conditioned media fraction is stored at −80° C. after collection. In certain aspects, the conditioned media fractions are thawed and pooled prior to isolating.

In certain aspects, the MSCs are further defined as bone marrow-derived MSCs. In particular aspects, the MSCs are further defined as adipose-derived MSCs.

In additional aspects, the method further comprises seeding the bioreactor with at least $1 \times 10^7$ MSCs prior to culturing the MSCs in the bioreactor. In some aspects, the MSCs are seeded at a density of about 400-500 cells/cm$^2$.

In certain aspects, the closed bioreactor is a hollow fiber bioreactor. In some aspects, the hollow fiber bioreactor is a Terumo cell expansion system.

In some aspects, the PLT is at a concentration of 5% in the media of the MSC culture. The concentration of the PLT may be about 2-10%, such as 3, 4, 5, or 6%. In certain aspects, fresh media is added continuously to the MSCs in the bioreactor. In particular aspects, the cells are cultured at 5% oxygen. In some aspects, culturing of step (a) is for 5-10 days, such as 6, 7, 8, or 9 days. In particular aspects, culturing of step (a) is for 8 days.

In certain aspects, the MSCs are cultured to 85-90% confluency, such as 85, 86, 87, 88, 89, or 90% confluency. Confluency may be measured by monitoring glucose and lactose levels. For example, levels of lactose may be about 2-6 mmol/L, such as about 2, 3, 4, 5, or 6 mmol/L and levels of glucose may be about 80-140 mg/dL, such as about 80, 85, 90, 95, 100, 105, 110, 115, 120, 125, 130, 135, or 140 mg/dL.

In some aspects, culturing in media essentially free of PLT is for 24-72 hours, such as 24-48, 36-50, 48-60, or 50-72 hours, such as about 36, 37, 38, 39, 40, 41, 42, 43, 44, 45, 46, 47, 48, 49, 50, 51, or 52 hours. In particular aspects, culturing is media essentially free of PLT is for about 48 hours. In particular aspects, the media of the further culturing step is free of PLT.

In certain aspects, the MSCs are washed between the culturing with PLT and the culturing in media essentially free or free of PLT. In some aspects, the MSCs are cultured in serum-free, defined media. In particular aspects, the complete method is performed under serum-free conditions.

In particular aspects, the conditioned media fractions are collected in sealed bags. In specific aspects, the conditioned media fractions are collected every 24-72 hours. In some aspects, the conditioned media fractions are collected every 40-50 hours. In one particular aspect, the conditioned media fractions are collected every 48 hours.

In some aspects, the conditioned media fractions are each 200-300 mL in volume, such as 200-250 or 250-300 mL. In certain aspects, the conditioned media fractions are collected for 10-14 days, such as 10, 11, 12, 13, or 14 days. In particular aspects, the conditioned media fractions are collected for 12 days. In specific aspects, at least 5 conditioned media fractions are collected. In specific aspects, the method is performed in less than 3 weeks.

In some aspects, each conditioned media fraction comprises $9 \times 10^{11}$ to $50 \times 10^{11}$ exosomes. In particular aspects, at least $10 \times 10^{12}$ exosomes are isolated in the collected media fractions. In specific aspects, at least $15 \times 10^{12}$ exosomes are isolated in the collected media fractions. At least $10 \times 10^{11}$, $15 \times 10^{11}$, $20 \times 10^{11}$, $25 \times 10^{11}$, $30 \times 10^{11}$, $35 \times 10^{11}$, $40 \times 10^{11}$, $45 \times 10^{11}$, $50 \times 10^{11}$, $60 \times 10^{11}$, $70 \times 10^{11}$, $80 \times 10^{11}$, $90 \times 10^{11}$, $10 \times 10^{12}$, $15 \times 10^{12}$, $20 \times 10^{12}$, or $25 \times 10^{12}$ exosomes may be isolated.

In certain aspects, isolating comprises filtration and ultracentrifugation of the pooled fractions to obtain an exosome-containing pellet and resuspending the exosome-containing pellet in a buffer. In some aspects, isolating is performed in a functionally-closed manner using a pump and heat-sealed tubing. In some aspects, filtration is further defined as passing the pooled fractions through a filter, such as a 0.2 µm filter. In additional aspects, isolating further comprises a centrifugation step prior to filtration to remove large cell debris. In particular aspects, isolating is performed at 4° C.

In specific aspects, the buffer comprises about 0.01-0.1 M, such as about 0.08, 0.09, or 0.1 M, particularly about 0.09 M Sodium Chloride, about 0.1-0.5 M, such as about 0.1, 0.2, or 0.3 M, particularly about 0.23 M Sodium Gluconate, about 0.1-0.5 M, such as about 0.1, 0.2, or 0.3 M, particularly about 0.27 M Sodium Acetate Trihydrate, 1-10 mM, such as about 6-7 mM, particularly about 5 mM Potassium Chloride, and about 1-5 mM, such as about 2-4 mM, particularly about 3 mM Magnesium Chloride. In some aspects, the buffer has a pH of about 6-8, such as about 6.8, 6.9, 7.0, 7.1, 7.2, 7.3, 7.4, 7.5, or 7.6, particularly about 7.4. In specific aspects, the buffer is PLASMALYTE-A®.

In additional aspects, the method further comprises loading the exosomes with a therapeutic agent. In some aspects, the therapeutic agent comprises one or more cytokines, chemotherapeutic drugs, nucleic acids, small molecules, or proteins. In certain aspects, the nucleic acids comprise DNA and/or RNA. In some aspects, the RNA is siRNA, miRNA, or shRNA. In particular aspects, the RNA is siRNA. In some aspects, loading comprises electroporating the exosomes. In certain aspects, electroporating is performed in PLASMA-LYTE-A®. In particular aspects, the method does not comprise washing the exosomes or exchanging buffers between the step of isolating exosomes and electroporating. In particular aspects, the number of exosomes from the step of isolating exosomes to the number of loaded exosomes does not decrease by more than 20%.

In another embodiment, there is provided a pharmaceutical composition comprising exosomes produced by the method of the embodiments (e.g., culturing the MSCs in a functionally closed bioreactor to 80-90% confluency in media comprising human platelet lysate (PLT); further culturing the cells in media essentially free of PLT (e.g., free of PLT); collecting conditioned media fractions from the bioreactor; and isolating exosomes from the conditioned media fractions).

In yet another embodiment, there is provided a method for treating cancer comprising administering an effective amount of the exosomes produced according to the methods of the embodiments (e.g., culturing the MSCs in a functionally closed bioreactor to 80-90% confluency in media comprising human platelet lysate (PLT); further culturing the cells in media essentially free of PLT (e.g., free of PLT); collecting conditioned media fractions from the bioreactor; and isolating exosomes from the conditioned media fractions). In some aspects, the subject is human.

In certain aspects, the electroporated exosomes are directly infused to the subject. In additional aspects, the method further comprises administering at least a second anti-cancer therapy. In some aspects, the at least a second anti-cancer therapy comprises chemotherapy, radiotherapy, gene therapy, surgery, hormonal therapy, anti-angiogenic therapy or immunotherapy.

In another embodiment, there is provided a method of delivering an RNA into a cell comprising administering an effective amount of RNA-loaded exosomes produced by the method of the embodiments (e.g., culturing the MSCs in a functionally closed bioreactor to 80-90% confluency in media comprising human platelet lysate (PLT); further culturing the cells in media essentially free of PLT (e.g., free of PLT); collecting conditioned media fractions from the bioreactor; isolating exosomes from the conditioned media fractions; and loading the isolated exosomes with RNA, thereby producing RNA-loaded exosomes). In some aspects, the cell is a human cell. In particular aspects, the cell is a cancer cell or a T cell.

In a further embodiment, there is provided a method of treating a disease or disorder in subject in need thereof comprising administering an effective amount of exosomes produced by the methods of the embodiments (e.g., culturing the MSCs in a functionally closed bioreactor to 80-90% confluency in media comprising human platelet lysate (PLT); further culturing the cells in media essentially free of PLT (e.g., free of PLT); collecting conditioned media fractions from the bioreactor; and isolating exosomes from the conditioned media fractions) to the subject. In some aspects, the exosomes are loaded with siRNA or miRNA. In specific aspects, the exosomes are loaded with KRAS siRNA. In some aspects, the subject is a human.

In some aspects, the disease or disorder is cancer, an inflammatory disorder, or an immune-associated disorder. In particular aspects, the cancer is lung cancer.

In certain aspects, the exosomes are administered orally, topically, intravenously, intraperitoneally, intramuscularly, endoscopically, percutaneously, subcutaneously, regionally, or by direct injection. In some aspects, the exosomes are administered intravenously.

In additional aspects, the method further comprises administering at least a second therapeutic agent. In some aspects, the at least a second therapeutic agent is an anti-cancer agent. In certain aspects, the anti-cancer agent is chemotherapy, radiotherapy, gene therapy, surgery, hormonal therapy, anti-angiogenic therapy or immunotherapy.

In another embodiment, there is provided a method of treating an immune-mediated inflammatory disease in a subject suffering from said disease, which comprises administering to said subject a therapeutically effective amount of the MSC-derived exosomes produced according to the present methods (e.g., culturing the MSCs in a functionally closed bioreactor to 80-90% confluency in media comprising human platelet lysate (PLT); further culturing the cells in media essentially free of PLT (e.g., free of PLT); collecting conditioned media fractions from the bioreactor; and isolating exosomes from the conditioned media fractions). In some aspects, the immune-mediated inflammatory disease is selected from the group consisting of rheumatoid arthritis (RA), Inflammatory Bowel Disease (IBD), and Crohn's disease. In certain aspects, the MSCs are allogeneic. In some aspects, the exosomes are administered systemically or locally. In certain aspects, the exosomes are administered via the rectal, nasal, buccal, vaginal, subcutaneous, intracutaneous, intravenous, intraperitoneal, intramuscular, intraarticular, intrasynovial, intrasternal, intrathecal, intralesional, or intracranial route, or via an implanted reservoir. In some aspects, the exosomes are administered in conjunction with at least one additional therapeutic agent.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1D: (FIG. 1A) Schematic procedure designed to produce EVs from mesenchymal stem cells (MSCs) using the Turumo Cell Expansion System (Bioreactor). (FIG. 1B) Schematic detailing the procedure for MSC bioreactor culture for collection of exosomes. (FIG. 1C) Schematic of the isolation and electroporation procedures of exosomes from MSC-conditioned media. (FIG. 1D) Schematic depicting the generation of MSC-derived exosomes.

(FIG. 4A) Flow cytometry of MSC-derived exosomes produced in the bioreactor on each harvest showing the expression of exosome markers. (FIG. 4B) Representative TEM from each collection showing the typical morphology of exosomes.

FIGS. 5A-5E: Quantification of exosomes produced in the bioreactor on each harvest. (FIG. 5A) Number of MSC-derived exosomes produced in the quantum determined by microBCA and Nanosight. (FIG. 5B) Particle size distribution of each harvest measure using Nanosight. (FIG. 5C) Levels of glucose and lactose in the bioreactor during the exosome production. (FIG. 5D) Number of exosomes produced per cell isolated from MSC-conditioned media at different times point and quantified by Nanosight. (FIG. 5E) Representative flow cytometry of exosome markers on MSC-derived exosomes isolated at 24 hours and 48 hours.

(FIG. 6A) Number of exosomes per cell isolated from conditioned media of MSC cultured with or without hPLT analyzed by Nanosight. (FIG. 6B) Flow cytometry of MSC-derived exosomes generated using media alone vs media supplemented with human platelet lysate (hPLT), showing the purity of exosomes produced on serum-free media.

(FIG. 8A) Efficiency of electroporation was evaluated by the apoptosis induced by siRNA delivery by MSC-derived exosomes on recipient cells after 48 hours. (FIG. 8B) Representative transmission electron micrograph of MSC exosomes, post-electroporation, using either research buffer (RB) or clinical buffer (CB; i.e., platelet lysate (PLT)) showing the maintenance of exosome integrity after electroporation. (FIG. 8C) Silencing of gene transcription in recipient cells induced by the delivery of siRNA using MSC-derived exosomes, which were electroporated using Lonza equipment and PLASMA-LYTE-A® solution.

DESCRIPTION OF ILLUSTRATIVE EMBODIMENTS

Figure 1A:
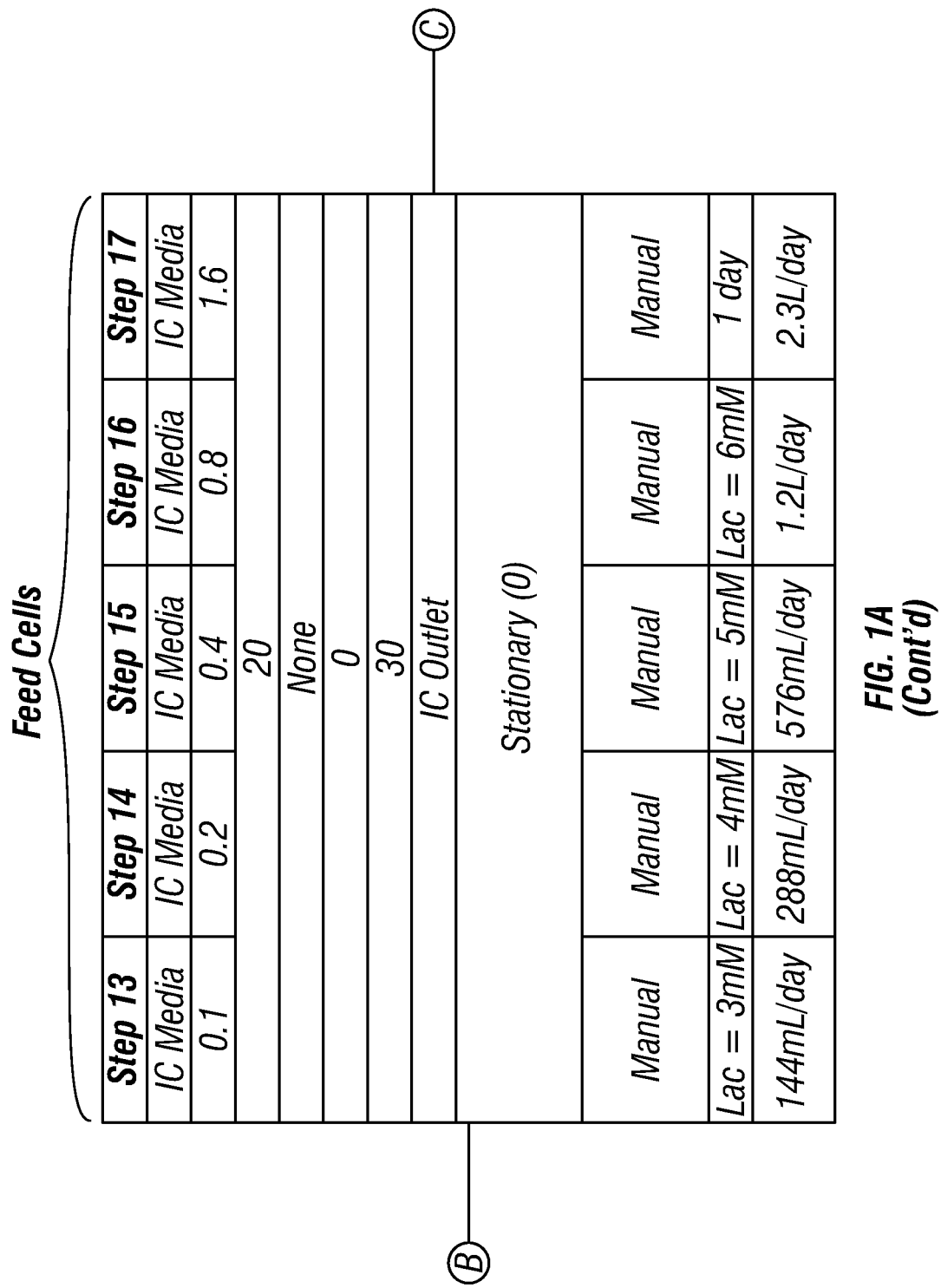

To formulate exosomes for human therapy, several aspects of their manufacture require careful consideration, including the large-scale production of exosomes in compliance with good manufacturing practice (GMP) standards. Thus, the present studies concerned the procedures and associated systematic analyses that were innovated to generate GMP-compliant exosomes.

Accordingly, in certain embodiments, the present disclosure provides an efficient and clinically relevant strategy to produce EVs, such as exosomes, from mesenchymal stromal cells (MSCs) using a functionally closed bioreactor, such as the Terumo Cell Expansion System. The method provided herein can yield at least $10 \times 10^{12}$ EVs in a short time, such as about 3 weeks. The present method includes the large-scale production and isolation of clinical grade EVs in a functionally-closed, serum-free system. The EVs are produced in clinically relevant doses, such as from bone marrow-derived MSCs.

In preferred embodiments, the entire method is serum-free and, thus, there is essentially no contamination of the MSC-derived EVs from exosomes in serum. Specifically, the method can comprise the use of human platelet lysate (PLT) in the initial culture of the MSCs in the bioreactor. The inventors have found that culturing the MSCs to about 80-90%, such as about 85% confluence, results in efficient production of EVs. Thus, the MSCs may then be switched to a PLT-free media for about 24-72 hours, such as about 24 hours or 48 hours, prior to collection of the conditioned media comprising the EVs. The conditioned media fractions may be collected about every 48 hours and frozen, such as about −80° C., until isolation of the EVs. The conditioned media fractions may be collected about 4-10 times, such as about 5, 6, 7, or 8 times, particularly about 6 times. Thus, the time period from seeding of the MSCs into the bioreactor until the final collection may be about 15-30 days, such as about 20 days. Each conditioned media fraction may comprise at least $9 \times 10^{11}$ exosomes, such as at least $1 \times 10^{12}$ exosomes, particularly about $3 \times 10^{12}$ exosomes.

Preferably, the collected media fractions are thawed and pooled prior to isolation of the EVs. The isolation of exosomes may comprise an initial centrifugation step, such as at 1,000 g, followed by ultracentrifugation, such as about 100,000 g. There may be multiple rounds of ultracentrifugation, such as 3 rounds, to produce an exosome pellet. In some aspects, the exosome pellet is resuspended in a GMP-compliant buffer, such as PLASMALYTE-A®. The exosomes may further be subjected to filtration, such as a 0.2 µm filter, prior to the ultacentrifugation. The method may result in production of total exosomes of at least $9\text{-}10 \times 10^{12}$, such as up to $15 \times 10^{12}$ exosomes or higher.

In addition, the exosomes may be loaded with therapeutic agents, such as cytokines, chemotherapeutics, or nucleic acids. Accordingly, there is provided a method for the loading of exosomes, such as those produced by the present methods, by electroporation in an FDA-approved buffer, such as PLASMALYTE-A®. The electroporation may be performed in a flow-through electroporation system, such as the 4D-Nucleofactor LV Large Scale Transfection System, Lonza). Each electroporation run may comprise at least 2×10$^{12}$ exosomes. The exosomes may be loaded with nucleic acids, such as siRNA. As the buffer is FDA-approved, sterile, and non-pyrogenic for use in patients, there is no washing step needed to exchange the buffer before administration to a patient as they may be directly infused into the patient. Thus, there is no loss of exosomes from the additional washing step as in prior methods which may result in a loss of about 50% of the exosomes. This buffer can maintain the integrity of the exosomes after electroporation.

Further provided herein are methods for use of the exosomes, such as exosomes loaded with siRNA, for the treatment of diseases, such as immune-related diseases and cancers, in patients.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

"Extracellular vesicles" and "EVs" are cell-derived and cell-secreted microvesicles which, as a class, include exosomes, exosome-like vesicles, ectosomes (which result from budding of vesicles directly from the plasma membrane), microparticles, microvesicles, shedding microvesicles (SMVs), nanoparticles and even (large) apoptotic blebs or bodies (resulting from cell death) or membrane particles.

As used herein, the terms "microvesicles" and "MVs" typically mean larger extracellular membrane vesicles or structures surrounded by a phospholipid bilayer that are about 100 nm to about 1,000 nm in diameter, or about 100 nm to about 400 nm in blood plasma. Microvesicles/MVs are formed by regulated release by budding or blebbing of the plasma membrane.

Within the class of extracellular vesicles, important components are "exosomes" themselves, which are preferably described as between about 40-120 nm, such as 50-100 nm in diameter and being membranous vesicles, i.e., vesicles surrounded by a phospholipid bilayer, of endocytic origin, which result from exocytic fusion, or "exocytosis" of multivesicular bodies (MVBs). Exosomes may be isolated from any suitable biological sample from a mammal, including but not limited to, whole blood, serum, plasma, urine, saliva, breast milk, cerebrospinal fluid, amniotic fluid, ascitic fluid, bone marrow and cultured mammalian cells (e.g. immature dendritic cells (wild-type or immortalized), induced and non-induced pluripotent stem cells, fibroblasts, platelets, immune cells, reticulocytes, tumor cells, mesenchymal stem cells, satellite cells, hematopoietic stem cells, pancreatic stem cells, white and beige pre-adipocytes and the like). As one of skill in the art will appreciate, cultured cell samples will be in the cell-appropriate culture media (using exosome-free serum).

Exosomes include specific surface markers not present in other vesicles, including surface markers such as tetraspanins, e.g., CD9, CD37, CD44, CD53, CD63, CD81, CD82 and CD151; targeting or adhesion markers such as integrins, ICAM-1, EpCAM, membrane fusion markers such as annexins, TSG101, ALIX; and other exosome transmembrane proteins such as Rab5b, HSP70, LAMP2 (lysosome-associated membrane protein) and LIMP (lysosomal integral membrane protein).

The term "mesenchymal stem cell" or "MSC", as used herein, refers to a multipotent somatic stem cell derived from mesoderm, having self-regenerating and differentiating capacity to produce progeny cells with a large phenotypic variety, including connective tissues, stroma of bone marrow, adipocytes, dermis and muscle, among others. MSCs generally have a cell marker expression profile characterized in that they are negative for the markers CD19, CD45, CD14 and HLA-DR, and positive for the markers CD105, CD106, CD90 and CD73. MSCs may be isolated from any type of tissue. Generally, MSCs may be isolated from bone marrow, adipose tissue, umbilical cord, or peripheral blood. In a particular embodiment, the MSC are bone marrow-derived stem cells.

The MSCs from which the exosomes derived can be autologous, allogeneic or xenogeneic. As used herein, the term "autologous" means that the donor of the MSCs and the recipient of the exosome (or isolated exosome population) derived from said MSCs are the same subject. The term "allogeneic" means that the donor of the MSCs and the recipient of the exosome (or isolated exosome population) derived from said MSCs are different subjects. The term "xenogeneic" means that the donor of the MSCs and the recipient of the exosome (or isolated exosome population) derived from said MSCs are subjects of different species. In a particular embodiment, the MSC's from which the exosomes derived are allogeneic.

The term "adipose tissue-derived stem cells" or "ASC", as used herein, refers to a MSC derived from adipose tissue. ASC can be isolated from adipose tissue by methods known in the art, for example the method described below under "Human adipose mesenchymal stem cells isolation and expansion". By "adipose tissue" it is meant any fat tissue. The adipose tissue may be brown or white adipose tissue, derived from, for example, subcutaneous, omental/visceral, mammary, gonadal, periorgan or other adipose tissue site. Preferably, the adipose tissue is subcutaneous white adipose tissue. The adipose tissue may comprise a primary cell culture or an immortalized cell line. The adipose tissue may be from any organism having fat tissue. In some embodiments, the adipose tissue is mammalian, and in further embodiments the adipose tissue is human. A convenient source of adipose tissue is liposuction surgery. However, it will be understood that neither the source of adipose tissue nor the method of isolation of adipose tissue is critical to the invention. In a particular embodiment, ASC are isolated from a lipoaspirate of a subject.

The MSCs can be derived from any animal, preferably a mammal including a non-primate (e.g., a cow, pig, horse, cat, dog, rat, or mouse) and a primate (e.g., a monkey, or a human). In a particular embodiment, the MSCs are human.

The term "functionally closed" refers to a system sealed to ensure fluid sterility either by hermetically sealing the entire system or by providing sterile barrier filters at all connections to the collection system The term "bioreactor" refers to a large-scale cell culture system that provides nutrients to cells and removes metabolites, as well as furnishes a physio-chemical environment conducive to cell growth, in a closed sterile system. In particular aspects, the biological and/or biochemical processes develop under monitored and controlled environmental and operating conditions, for example, pH, temperature, pressure, nutrient supply and waste removal. According to the present disclosure, the basic class of bioreactors suitable for use with the present methods includes hollow fiber bioreactors.

The term "hollow fiber" is intended to include hollow structures (of any shape) containing pores of defined size, shape and density for use in delivering nutrients (in solution) to cells contained within a bioreactor and for removal of waste materials (in solution) from cells contained within a bioreactor. For purposes of the present disclosure, hollow fibers may be constructed of a resorbable or nonresorbable material. Fibers include, but are not limited to, tubular structures.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to affect such treatment or prevention of the disease.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The terms "contacted" and "exposed," when applied to a cell, are used herein to describe the process by which a therapeutic agent is delivered to a target cell or are placed in direct juxtaposition with the target cell. To achieve cell killing, for example, one or more agents are delivered to a cell in an amount effective to kill the cell or prevent it from dividing.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

A "therapeutic agent" as used herein refers to any agent that can be administered to a subject for the purpose of obtaining a therapeutic benefit of a disease or health-related condition. For example, nanoparticles that include a therapeutic agent may be administered to a subject for the purpose of reducing the size of a tumor, reducing or inhibiting local invasiveness of a tumor, or reducing the risk of development of metastases.

A "diagnostic agent" as used herein refers to any agent that can be administered to a subject for the purpose of diagnosing a disease or health-related condition in a subject. Diagnosis may involve determining whether a disease is present, whether a disease has progressed, or any change in disease state.

The therapeutic or diagnostic agent may be a small molecule, a peptide, a protein, a polypeptide, an antibody, an antibody fragment, a DNA, or an RNA. In particular embodiments, the therapeutic or diagnostic agent is a siRNA.

A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may formed by partial or substantial complementary binding. Thus, a nucleic acid may encompass a double-stranded molecule that comprises one or more complementary strand(s) or "complement(s)" of a particular sequence, typically comprising a molecule. As used herein, a single stranded nucleic acid may be denoted by the prefix "ss" and a double stranded nucleic acid by the prefix "ds".

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art.

The term "siRNA" (short interfering RNA) refers to short double stranded RNA complex, typically 19-28 base pairs in length. In other words, siRNA is a double-stranded nucleic acid molecule comprising two nucleotide strands, each strand having about 19 to about 28 nucleotides (i.e., about 19, 20, 21, 22, 23, 24, 25, 26, 27, or 28 nucleotides). The complex often includes a 3'-overhang. siRNA can be made using techniques known to one skilled in the art and a wide variety of siRNA is commercially available from suppliers such as Integrated DNA Technologies, Inc. (Coralville, Iowa). In one embodiment, a 2'-O-methyl-modified siRNA duplex against TNF-α as described herein can be incorporated into the nanoparticles, wherein the 2'-O-methyl modification on the anti-sense strand eliminates off-target effects, minimizes nonspecific immune responses, and improves siRNA stability.

A "microRNA (miRNA)" is short, non-coding RNAs that can target and substantially silence protein coding genes through 3'-UTR elements. miRNAs can be approximately 21-22 nucleotides in length and arise from longer precursors, which are transcribed from non-protein-encoding genes.

An "immune disorder," "immune-related disorder," or "immune-mediated disorder" refers to a disorder in which the immune response plays a role in the development or progression of the disease Immune-mediated disorders include autoimmune disorders, allograft rejection, graft versus host disease and inflammatory and allergic conditions.

An "autoimmune disease" refers to a disease in which the immune system produces an immune response (for example, a B-cell or a T-cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

The term "confluency" as used herein refers to the percentage of cells covering a surface, such as the hollow fibers of a bioreactor. The confluency may be measured by levels of glucose and/or lactose in the media in which the cells are cultured.

II. Production of Exosomes

Certain embodiments of the present disclosure concern methods for the large-scale production of clinical grade EVs, particularly exosomes, through the use of a functionally closed system, such as a bioreactor, particularly a hollow fiber bioreactor. Importantly, the entire process of exosomes production, including subsequent loading with therapeutic agents, may be serum-free.

A. Mesenchymal Stem Cells

The cells for production of the EVs may be MSCs, such as adipose-derived or bone-marrow derived MSCs. In particular aspects, the MSCs are human MSCs, which may autologous or allogeneic.

The MSCs may be seeded in the bioreactor at a density of about 100-1,000 cells/cm$^2$, such as about 150 cells/cm$^2$, about 200 cells/cm$^2$, about 250 cells/cm$^2$, about 300 cells/cm$^2$, such as about 350 cells/cm$^2$, such as about 400 cells/cm$^2$, such as about 450 cells/cm$^2$, such as about 500 cells/cm$^2$, such as about 550 cells/cm$^2$, such as about 600 cells/cm$^2$, such as about 650 cells/cm$^2$, such as about 700 cells/cm$^2$, such as about 750 cells/cm$^2$, such as about 800 cells/cm$^2$, such as about 850 cells/cm$^2$, such as about 900 cells/cm$^2$, such as about 950 cells/cm$^2$, or about 1000 cells/cm$^2$. Particularly, the cells may be seeded at a cell density of about 400-500 cells/cm$^2$, such as about 450 cells/cm$^2$.

The total number of cells seeded in the bioreactor may be about $1.0 \times 10^6$ to about $1.0 \times 10^8$ cells, such as about $1.0 \times 10^6$ to $5.0.0 \times 10^6$, $5.0 \times 10^6$ to $1.0 \times 10^7$, $1.0 \times 10^7$ to $5.0 \times 10^7$, $5.0 \times 10^7$ to $1.0 \times 10^8$ cells. In particular aspects, the total number of cells seeded in the bioreactor are about $1.0 \times 10^7$ to about $3.0 \times 10^7$, such as about $2.0 \times 10^7$ cells.

The cells may be seeded in any suitable cell culture media, many of which are commercially available. Exemplary media include DMEM, RPMI, MEM, Media 199, HAMS and the like. In one embodiment, the media is alpha MEM media, particularly alpha MEM supplemented with L-glutamine. The media may be supplemented with one or more of the following: growth factors, cytokines, hormones, or B27, antibiotics, vitamins and/or small molecule drugs. Particularly, the media may be serum-free.

In some embodiments the cells may be incubated at room temperature. The incubator may be humidified and have an atmosphere that is about 5% $CO_2$ and about 1% 02. In some embodiments, the $CO_2$ concentration may range from about 1-20%, 2-10%, or 3-5%. In some embodiments, the $O_2$ concentration may range from about 1-20%, 2-10%, or 3-5%.

In particular embodiments, the cells are seeded and cultured in serum-free media. The media may be supplement with platelet lysate, particularly human platelet lysate (PLT). The PLT may be present in the media at a concentration of about 1-10%, such as about 1-4%, 2-5%, 3-6%, 4-7%, 5-8%, or 6-10%, such as about 4%, 5%, or 6%, particularly about 5%.

The MSCs may be initially cultured in the bioreactor for about 5-10 days after seeding, such as about 5, 6, 7, 8, 9, or 10 days, particularly about 7, 8, or 9 days. Specifically, the MSCs may be initially cultured in the media with PLT until about 75-95% confluency, such as about 75-80%, 80-85%, 85-90%, or 90-95% confluency, particularly about 85-90%, such as 85%, 86%, 87%, 88%, 89%, or 90% confluency. Once the cells reach the intended confluency, the cells may be switched to a media that is free of PLT. The cells may be washed with a buffer, such as PBS, at least once prior to transfer to the PLT-free media.

The culture of the cells in the PLT-free media is used to prevent contamination or dilution of the MSC-derived exosomes with exosomes that may be present in the PLT. In some aspects, the PLT may be subjected to centrifugation to remove exosomes and obtain an exosome-free PLT.

The cells may be cultured in the PLT-free media for about 8-100 hours, such as 12-72 hours, such as about 12-15, 15-20, 20-25, 25-30, 35-40, 40-45, 45-50, 50-55, 55-60, 65-70, or 70-72 hours. Particularly, the cells may be cultured in the PLT-free media for about 24-48 hours, such as about 48 hours before harvesting of the exosomes.

B. Bioreactor

Bioreactors can be grouped according to general categories including: static bioreactors, stirred flask bioreactors, rotating wall vessel bioreactors, hollow fiber bioreactors and direct perfusion bioreactors. Within the bioreactors, cells can be free, or immobilized, seeded on porous 3-dimensional scaffolds (hydrogel).

Hollow fiber bioreactors can be used to enhance the mass transfer during culture. A Hollow fiber bioreactor is a 3D cell culturing system based on hollow fibers, which are small, semi-permeable capillary membranes arranged in parallel array with a typical molecular weight cut-off (MWCO) range of 10-30 kDa. These hollow fiber membranes are often bundled and housed within tubular polycarbonate shells to create hollow fiber bioreactor cartridges. Within the cartridges, which are also fitted with inlet and outlet ports, are two compartments: the intracapillary (IC) space within the hollow fibers, and the extracapillary (EC) space surrounding the hollow fibers.

Thus, for the present disclosure, the bioreactor may be a hollow fiber bioreactor. Hollow fiber bioreactors may have the cells embedded within the lumen of the fibers, with the medium perfusing the extra-lumenal space or, alternatively, may provide gas and medium perfusion through the hollow fibers, with the cells growing within the extralumenal space. Hollow fiber bioreactors suitable for the present disclosure are known in the art and may include, but are not limited to, the Caridian (Terumo) BCT Quantum Cell Expansion System.

The hollow fibers should be suitable for the delivery of nutrients and removal of waste in the bioreactor. The hollow fibers may be any shape, for example, they may be round and tubular or in the form of concentric rings. The hollow fibers may be made up of a resorbable or non-resorbable membrane. For example, suitable components of the hollow fibers include polydioxanone, polylactide, polyglactin, polyglycolic acid, polylactic acid, polyglycolic acid/trimethylene carbonate, cellulose, methylcellulose, cellulosic polymers, cellulose ester, regenerated cellulose, pluronic, collagen, elastin, and mixtures thereof.

The bioreactor may be primed prior to seeding of the cells. The priming may comprise flushing with a buffer, such as PBS. The priming may also comprise coating the bioreactor with an extracellular matrix protein, such as fibronectin. The bioreactor may then be washed with PLT media, such as alpha MEM.

C. Conditioned Media Collection

The conditioned media from the cells cultured in PLT-free media may be collected every 8-100 hours, such as every 12-72 hours, such as about 12-15, 15-20, 20-25, 25-30, 35-40, 40-45, 45-50, 50-55, 55-60, 65-70, or 70-72 hours. Particularly, the conditioned media fractions may be collected every about 24-48 hours.

The conditioned media fractions may comprise a volume of about 100-500 mL, such as about 100-150, 150-200, 250-300, 350-400, 400-450, or 450-500 mL, particular about 250 mL. The fractions may be collected in sealed bags and cryopreserved, such as at about −70° to about −90° C., such as about −80° C. until isolation of the exosomes.

In particular aspects, the conditioned media is collected at least 4 times, such as 4-10 times, particularly 5, 6, 7, 8, or 9 times, specifically 6 times for each run. The individual fractions may be thawed, such as at 4° C. overnight, such as at 2-6° C. for about 10-20 hours.

D. Isolation of Exosomes

The pooled conditioned media fractions may then be subjected to exosome isolation, particularly at 4° C. The conditioned media may be centrifuged at about a temperature of 2° C., 4° C., 6° C., 8° C., 10° C., 12° C., 14° C., 16° C., 18° C., 20° C., 22° C., 24° C., or 26° C. In one embodiment, the conditioned media is centrifuged at about a temperature of 4° C. The exosome isolation may be performed by methods known in the art for exosome isolation. Preferably, the isolation of exosomes is also performed in a closed system as the above production of exosomes. This may be accomplished through the use of pumps and sealed tubing.

The isolation may comprise a centrifugation step to remove large debris, followed by filtration, and one or more ultracentrifugation steps. The isolation method may be performed multiple times to process all of the pooled media fractions, such as 3 times.

The centrifugation step may comprise centrifugation at about 500-2,000 g, such as about 1,000 g, for about 5-25 min, such as about 15 min. The conditioned media may be centrifuged at about 1,000 g, 2,000 g, 4,000 g, 6,000 g, 8,000 g; 10,0000 g; 12,000 g, 14,000 g, 16,000 g, or 18,000 g. The centrifugation may be for a period of time such as 10-30 minutes, 12-28 minutes, 14-24 minutes, or 15-20 minutes. As one of skill in the art will appreciate, a suitable commercially available laboratory centrifuge, e.g., THERMO-SCIENTIFIC™ or COLE-PARMER™, is employed to conduct this centrifugation step. In particular, the centrifugation may be performed in a closed system, such as the Cobe 2991 Cell Processor (Terumo). The low-speed centrifugation may be performed more than once to remove live cells, dead cells, and larger cellular debris.

The filtration step may comprise use of a filtering bag with a submicron filter, such as a 0.1-0.3 micron filter, such as a 0.2 micron filter, such as to remove debris, such as larger microvesicles. The supernatant may then be transferred to tubes (e.g., polycarbonate tube) using syringes a line connected directly with the tubes. The filtration may be repeated more than once. The filtration may be conducted by one or more passes through filters of the same size, for example, a 0.2 micron filter. Alternatively, filtration using 2 or more filters may be conducted, using filters of the same or of decreasing sizes, e.g. one or more passes through a 40-50 micron filter, one or more passes through a 20-30 micron filter, one or more passes through a 10-20 micron filter, one or more passes through a 0.2-10 micron filter, etc. Suitable filters for use in this step include the use of 0.45 and 0.22 micron filters.

The ultracentrifugation may be performed at 75,000 to 150,000 g, such as 100,000 to 170,000 g such as about 100,000 g for about 2-6 hours, such as 1-3 hours, such as about 4 or 5 hours. Any commercially available ultracentrifuge, e.g., THERMO-SCIENTIFIC™ or Beckman™, may be employed to conduct this step. Specifically, the ultracentrifugation may be performed using any closed-system centrifuge such as, but not limited to, the type 45 Ti rotor (Beckman-Coulter). This ultracentrifugation step may optionally be repeated, e.g., 2 or more times, in order to enhance results. The exosome-containing pellet is removed from the supernatant using established techniques and resuspended in a suitable physiological solution.

As one of skill in the art will appreciate, the exosome pellet from any of the centrifugation or ultracentrifugation steps may be washed between centrifugation steps using an appropriate physiological solution, e.g., sterile PBS, sterile 0.9% saline or sterile carbohydrate-containing 0.9% saline buffer.

After centrifugation, the solution is removed and the exosomes are resuspended in a suitable buffer such as PBS. The pH of the buffer may be any pH that is compatible with the sample, but a typical range is from 6 to 8. The buffer may have a pH from 4 to 10, 4 to 6, 4 to 8, 6 to 10, 6 to 8, or 8 to 10. In particular, the exosome pellet may be resuspended in a clinical grade buffer, such as PLASMALYTE-A®, such as at a physiological pH of about 7.4. The volume of buffer may be about 0.01 volumes to about 0.09 volumes, about 0.02 volumes to about 0.08 volumes; about 0.03 volumes to about 0.07 volumes of the precipitating solution. The harvested exosomes may be used immediately, such as for electroporation or therapy, or frozen and stored, e.g., at −20° C., for later use.

As used herein, analysis includes any method that allows direct or indirect visualization of exosomes and may be in vivo or ex vivo. For example, analysis may include, but not limited to, ex vivo microscopic or cytometric detection and visualization of exosomes bound to a solid substrate, flow cytometry, fluorescent imaging, and the like. In an exemplary aspect, cancer cell-derived exosomes are detected using antibodies directed to glypican 1 and subsequently bound to a solid substrate and visualized using microscopic or cytometric detection. The exosomes may be analyzed by flow cytometric expression of the exosome surfaces markers: CD63, CD47, CD9 and CD81, and/or transmission electron microscopy (TEM). Additionally, nanoparticle tracking analysis and microBCA assay may be used to quantitate the exosomes.

Thus, the time period from seeding of the MSCs into the bioreactor until the final collection may be about 15-30 days, such as 16, 17, 18, 19, 20, 21, 22, 23, or 24 days, such as about 19 or 20 days. Each conditioned media fraction may comprise at least $9 \times 10^{11}$ exosomes, such as at least $1 \times 10^{12}$ exosomes, such as at least $2 \times 10^{12}$ exosomes, particularly about $3 \times 10^{12}$ exosomes. The method may result in production of total exosomes of at least $10 \times 10^{12}$ exosomes, such as at least $11 \times 10^{12}$ exosomes, such as at least $12 \times 10^{12}$ exosomes, such as at least $13 \times 10^{12}$ exosomes, such as at least $14 \times 10^{12}$ exosomes, such as at least $15 \times 10^{12}$ exosomes, such as at least $16 \times 10^{12}$ exosomes, such as at least $17 \times 10^{12}$ exosomes, such as at least $18 \times 10^{12}$ exosomes, such as at least $19 \times 10^{12}$ exosomes, or such as at least $20 \times 10^{12}$ exosomes.

E. Loading of Exosomes

The exosomes produced by the present methods may be loaded with cargo, such as therapeutic agents or diagnostic agents. Examples of cargo that may be delivered using the present exosomes include exogenous materials that do not exist naturally in exosomes (originate from an external source), such as, but not limited to, nucleic acid molecules such as DNA (both nuclear and mitochondrial), RNA such as mRNA, tRNA, miRNA, and siRNA, aptamers and other nucleic acid-containing molecules, peptides, proteins, ribozymes, carbohydrates, polymers, therapeutics, small molecules and the like.

In one embodiment, the present isolated exosomes are particularly useful for the delivery of compounds having a secondary structure (e.g., miRNA, mRNA, protein/peptide), as well as large compounds, e.g., nucleic acid molecules which comprising more than 20 base pairs, e.g., more than 50 base pairs or more than 100 base pairs, peptides, proteins, and the like.

Cargo may be introduced into the present exosomes using methods established in the art for introduction of cargo into cells. Thus, cargo may be introduced into exosomes, for example, using electroporation applying voltages in the range of about 20-1000 V/cm.

Transfection using cationic lipid-based transfection reagents may also be used to introduce cargo into exosomes. Examples of suitable transfection reagents include, but are not limited to, Lipofectamine MessengerMAX™ Transfection Reagent, Lipofectamine RNAiMAX Transfection Reagent, Lipofectamine 3000 Transfection Reagent, or Lipofectamine LTX Reagent with PLUS™ Reagent. For cargo loading, a suitable amount of transfection reagent is used and may vary with the reagent, the sample and the cargo. For example, using Lipofectamine MessengerMAX™ Transfection Reagent, an amount in the range of about 0.15 uL to 10 uL may be used to load 100 ng to 2500 ng mRNA or protein into exosomes. Other methods may also be utilized to introduce cargo into exosomes, for example, the use of cell-penetrating peptides for protein introduction.

In particular embodiments, the cargo, such as nucleic acids, such as siRNA, is loaded into the exosomes using electroporation, such as by electroporation in an FDA-approved buffer, such as PLASMALYTE-A®. The electroporation may be performed in a flow-through electroporation system, such as the 4D-Nucleofactor LV Large Scale Transfection System, Lonza). Each electroporation run may comprise at least $2 \times 10^{12}$ exosomes. As the buffer is FDA-approved, sterile, and non-pyrogenic for use in patients, there is no washing step needed to exchange the buffer before administration to a patient as they may be directly infused into the patient. Thus, there is no loss of exosomes from the additional washing step as in prior methods which may result in a loss of about 50% of the exosomes.

In particular embodiments, the therapeutic agent may be RNA, such as siRNA, shRNA, plasmid, mRNA, miRNA, or ncRNA, particularly siRNA or miRNA therapeutics. The miRNA may be a miRNA mimic, or a miRNA precursor. The size of the RNA loaded into the exosomes may be less than 100 nucleotides in length, such as less than 75 nucleotides, particularly less than 50 nucleotides in length. For example, the RNA may have a length of about 10-100 nucleotides, such as 20-50 nucleotides, particularly 10-20, 15-25, 20-30, 25-35, 30-40, or 45-50 nucleotides.

The RNA may be modified or non-modified. The RNA may comprise an alteration of one or more nucleotides. Such alterations can include the addition of non-nucleotide material, such as to the end(s) of the RNA or internally (at one or more nucleotides of the RNA). In certain aspects, the RNA molecule contains a 3'-hydroxyl group. Nucleotides in the RNA molecules of the present disclosure can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication No. 20040019001 and U.S. Pat. No. 6,673,611 (each of which is incorporated by reference in its entirety). Collectively, all such altered nucleic acids or RNAs described above are referred to as modified siRNAs.

Preferably, RNAi is capable of decreasing the expression of a protein by at least 10%, 20%, 30%, or 40%, more preferably by at least 50%, 60%, or 70%, and even more preferably by at least 75%, 80%, 90%, 95% or more.

The siRNA as used in the methods or compositions described herein may comprise a portion which is complementary to an mRNA sequence encoded by NCBI Reference Sequence for the stated genes/proteins. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. In an embodiment, the overhang is UU. The siRNA can be 5' phosphorylated or not and may be modified with any of the known modifications in the art to improve efficacy and/or resistance to nuclease degradation. In a non-limiting embodiment, the siRNA can be administered such that it is transfected into one or more cells. In one embodiment, a siRNA may comprise a double-stranded RNA comprising a first and second strand, wherein one strand of the RNA is 80, 85, 90, 95 or 100% complementary to a portion of an RNA transcript of a gene.

In one embodiment, a single strand component of a siRNA of the present disclosure is from 14 to 50 nucleotides in length. In another embodiment, a single strand component of a siRNA is 14, 15, 16, 17, 18, 19, 20, 21, 22, 23, 24, 25, 26, 27, or 28 nucleotides in length. In yet another embodiment, a single strand component of a siRNA of the present disclosure is 21 nucleotides in length. In yet another embodiment, a single strand component of a siRNA of the present disclosure is 22 nucleotides in length. In yet another embodiment, a single strand component of a siRNA of the present disclosure is 23 nucleotides in length. In one embodiment, a siRNA of the present disclosure is from 28 to 56 nucleotides in length.

A target gene generally means a polynucleotide comprising a region that encodes a polypeptide, or a polynucleotide region that regulates replication, transcription or translation or other processes important to expression of the polypeptide, or a polynucleotide comprising both a region that encodes a polypeptide and a region operably linked thereto that regulates expression. The targeted gene can be chromosomal (genomic) or extrachromosomal. It may be endogenous to the cell, or it may be a foreign gene (a transgene). The foreign gene can be integrated into the host genome, or it may be present on an extrachromosomal genetic construct such as a plasmid or a cosmid. The targeted gene can also be derived from a pathogen, such as a virus, bacterium, fungus or protozoan, which is capable of infecting an organism or cell. Target genes may be viral and pro-viral genes that do not elicit the interferon response, such as retroviral genes. The target gene may be a protein-coding gene or a non-protein coding gene, such as a gene which codes for ribosomal RNAs, splicosomal RNA, tRNAs, etc.

Any gene being expressed in a cell can be targeted. Preferably, a target gene is one involved in or associated with the progression of cellular activities important to disease or of particular interest as a research object. Thus, by way of example, the following are classes of possible target genes that may be used in the methods of the present disclosure to modulate or attenuate target gene expression: developmental genes (e.g., adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), tumor suppressor genes (e.g., APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, ras, MMAC1, FCC, MCC, FUS1, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide), pro-apoptotic genes (e.g., CD95, caspase-3, Bax, Bag-1, CRADD, TSSC3, bax, hid, Bak, MKP-7, PARP, bad, bcl-2, MST1, bbc3, Sax, BIK, and BID), cytokines (e.g., GM-CSF, G-CSF, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 IFN-α, IFN-β, IFN-γ, MIP-1α, MIP-1β, TGF-β, TNF-α, TNF-β, PDGF, and mda7), oncogenes (e.g., ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TALL TCL3 and YES), and enzymes (e.g., ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, pectinesterases, peroxidases, phosphatases, phospholipases, phophorylases, polygalacturonases, proteinases and peptidases, pullanases, recombinases, reverse transcriptases, topoisomerases, xylanases).

As will be appreciated by one of skill in the art, prior or subsequent to loading with cargo, the present exosomes may be further altered by inclusion of a targeting moiety to enhance the utility thereof as a vehicle for delivery of cargo. In this regard, exosomes may be engineered to incorporate an entity that specifically targets a particular cell to tissue type. This target-specific entity, e.g. peptide having affinity for a receptor or ligand on the target cell or tissue, may be integrated within the exosomal membrane, for example, by fusion to an exosomal membrane marker using methods well-established in the art.

III. Methods of Use

In some embodiments, the present disclosure provides methods of using the exosomes provided herein for the delivery of a therapeutic agent, such as RNAi, to a cell. Additional immune cells that may be targeted by the exosomes for delivery include dendritic cells, NK cells, and/or B cells. In further embodiments, the therapeutic agent delivered by the exosomes of the present disclosure may be a small molecule, peptide, vaccine, or an antigen. The cell may be in vivo or ex vivo. In one embodiment, there is provided a method of delivering RNA into a cell comprising administering an effective amount of exosomes comprising RNAi to the cell. The cell may be an immune cell, such as a T cell, or a cancer cells, such as KRAS-positive cancer cells.

In a further embodiment, there is provided a method of immunostimulating an organism comprising administering an effective amount of exosomes encapsulating RNA to the subject. The RNA may be an immune-modulatory RNA. In another embodiment, there is provided a method of treating a subject with a disease or disorder comprising administering an effective amount of the exosomes of the present disclosure. In some embodiments, there is provided the use of the exosomes of the present disclosure for the treatment of a disease or disorder or for immunostimulating a subject.

The in vivo cell can be in any subject, such as a mammal. For example, the subject may be a human, a mouse, a rat, a rabbit, a dog, a cat, a cow, a horse, a pig, a goat, a sheep, a primate, or an avian species. In particular embodiments, the subject is a human. For example, the human may be a subject with a disease. The disease may be any disease that afflicts a subject, such as an inflammatory disease, a hyperproliferative disease, an infectious disease, or a degenerative disease. In particular embodiments, the disease is a hyperproliferative disease such as cancer. For example, the cancer may be breast cancer, lung cancer, prostate cancer, ovarian cancer, brain cancer cell, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, intestinal cancer, lymphoma, or leukemia. In particular embodiments, the cancer is ovarian cancer.

In another embodiment, there is provided a method of treating an immune-mediated inflammatory disease in a subject suffering from said disease, which comprises administering to said subject a therapeutically effective amount of the exosomes of the present disclosure.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, there is provided a method of treating a disease or disorder in a subject comprising administering an effective amount of exosomes loaded with a therapeutic agent to a subject in need thereof. The disease may be an immune-associated disease, such as an autoimmune disease. Non-limiting examples of autoimmune diseases include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or mebranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/ giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type I diabetes mellitus, Crohn's disease; ulcerative colitis, myasthenia gravis, glomerulonephritis, ankylosing spondylitis, vasculitis, or psoriasis. The subject can also have an allergic disorder such as Asthma.

Treatment outcomes can be predicted and monitored and/or patients benefiting from such treatments can be identified or selected via the methods described herein.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, the patient's clinical history and response to the agent, and the discretion of the attending physician. The agent is suitably administered to the patient at one time or over a series of treatments.

Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

The exosomes described herein may be used in therapeutic, research and diagnostic applications. For example the exosomes described infra may be added to a cell culture to enhance one or more phenotypic traits of the cells. The exosomes of the invention may be added to a cell culture to inhibit one or more phenotypic traits of the cells. The exosomes of the invention may be added to a cell culture to provide a new phenotypic trait of the cells.

A. Pharmaceutical Compositions

Certain of the methods set forth herein pertain to methods involving the administration of a pharmaceutically effective amount of a composition comprising exosomes of the present disclosure.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present disclosure may comprise different types of carriers depending on whether it is to be administered in solid, liquid or aerosol form, and whether it need to be sterile for such routes of administration as injection.

The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations preferably meet sterility, pyrogenicity, general safety and purity standards as required by FDA Office of Biologics standards.

The compositions comprising exosomes may be extensively dialyzed to remove undesired small molecular weight molecules and/or lyophilized for more ready formulation into a desired vehicle, where appropriate. In particular aspects, the compositions comprising exosomes (e.g., in PLASMALYTE-A®) of the present disclosure do not required any processing and may be directly infused to the subject. The active compounds will then generally be formulated for administration by any known route, such as parenteral administration. Methods of administration are discussed in greater detail below.

The present disclosure contemplates methods using compositions that are sterile solutions for intravascular injection or for application by any other route as discussed in greater detail below. A person of ordinary skill in the art would be familiar with techniques for generating sterile solutions for injection or application by any other route. Sterile injectable solutions are prepared by incorporating the active compounds in the required amount in the appropriate solvent with various of the other ingredients familiar to a person of skill in the art.

The formulation of the composition may vary depending upon the route of administration. For parenteral administration in an aqueous solution, for example, the solution should be suitably buffered and the liquid diluent first rendered isotonic with sufficient saline or glucose. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, formulations for administration via an implantable drug delivery device, and any other form. One may also use nasal solutions or sprays, aerosols or inhalants in the present disclosure.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. A person of ordinary skill in the art would be familiar with well-known techniques for preparation of oral formulations.

In certain embodiments, pharmaceutical composition includes at least about 0.1% by weight of the active agent. The composition may include, for example, about 0.01%. In other embodiments, the pharmaceutical composition includes about 2% to about 75% of the weight of the composition, or between about 25% to about 60% by weight of the composition, for example, and any range derivable therein.

The pharmaceutical composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition may be stable under the conditions of manufacture and storage, and preserved against the contaminating action of microorganisms, such as bacteria and fungi. It will be appreciated that exotoxin contamination should be kept minimally at a safe level, for example, less than 0.5 ng/mg protein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, one may use nasal solutions or sprays, aerosols or inhalants in the present disclosure. Nasal solutions may be aqueous solutions designed to be administered to the nasal passages in drops or sprays.

Sterile injectable solutions are prepared by incorporating the nanoparticles in the required amount in the appropriate solvent with various of the other ingredients enumerated above, as required, followed by sterilization.

Upon formulation, exosomes will be administered in a manner compatible with the dosage formulation and in such amount as is therapeutically effective.

The nanoparticles can be administered to the subject using any method known to those of ordinary skill in the art. For example, a pharmaceutically effective amount of a composition comprising exosomes may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990). In particular embodiments, the composition is administered to a subject using a drug delivery device.

In other embodiments, exosomes are formulated for administration by routes including, but not limited to, oral, intranasal, enteral, topical, sublingual, intra-arterial, intramedullary, intrathecal, inhalation, ocular, transdermal, vaginal or rectal routes, and will include appropriate carriers in each case. For example, exosome compositions for topical application may be prepared including appropriate carriers. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered, for example, anti-microbial agents, anti-oxidants and other preservatives may be added to the composition to prevent microbial growth and/or degradation over prolonged storage periods.

A pharmaceutically effective amount of the nanoparticles is determined based on the intended goal, for example inhibition of cell death. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

For example, a dose of the therapeutic agent may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, the method may provide a continuous supply of a pharmaceutical composition to the patient. This could be accomplished by catheterization, followed by continuous administration of the therapeutic agent. The administration could be intra-operative or post-operative.

B. Combination Therapies

Certain embodiments of the present disclosure provide for the administration or application of one or more secondary forms of therapies for the treatment or prevention of a disease. For example, the disease may be a hyperproliferative disease, such as cancer.

The secondary form of therapy may be administration of one or more secondary pharmacological agents that can be applied in the treatment or prevention of cancer.

If the secondary therapy is a pharmacological agent, it may be administered prior to, concurrently, or following administration of the nanoparticles.

The interval between the administration of the exosomes and the secondary therapy may be any interval as determined by those of ordinary skill in the art. For example, the interval may be minutes to weeks. In embodiments where the agents are separately administered, one would generally ensure that a long period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations the time period for treatment may be extended, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the nanoparticles.

Various combinations may be employed. For the example below an exosome composition is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present disclosure to a patient will follow general protocols for the administration of such compounds, taking into account the toxicity, if any, of the agents. Therefore, in some embodiments there is a step of monitoring toxicity that is attributable to combination therapy. It is expected that the treatment cycles may be repeated. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma1I and calicheamicin omega1I); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dronanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabien; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, may rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell may bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds; cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication No. WO2015016718; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156, can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryo-surgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. Further examples can therefore be contemplated. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Kits

In various aspects of the embodiments, a kit is envisioned containing therapeutic agents and/or other therapeutic and delivery agents. In some embodiments, the present embodiments contemplates a kit for preparing and/or administering an exosome composition of the embodiments. The kit may comprise one or more sealed vials containing any of the pharmaceutical compositions of the present embodiments. The kit may include, for example, exosomes as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production and Characterization of Exosomes

To generate large amounts of exosomes from MSCs, a bioreactor culture of bone marrow-derived MSCs was adapted to enable the harvest of 250 mL collections of conditioned media. The Terumo Quantum Cell Expansion system is an automated hollow fiber cell culture platform designed for GMP compatible production of cells.

The MSCs were seeded in the bioreactor at a density of approximately 450 cells/cm$^2$ with approximately $2.0 \times 10^7$ MSCs. The cells were cultured for 8 days in 5% oxygen using alpha MEM medium supplemented with L-glutamine plus the human platelet lysate (PLT) for MSC expansion and adherence.

Figure 1C:
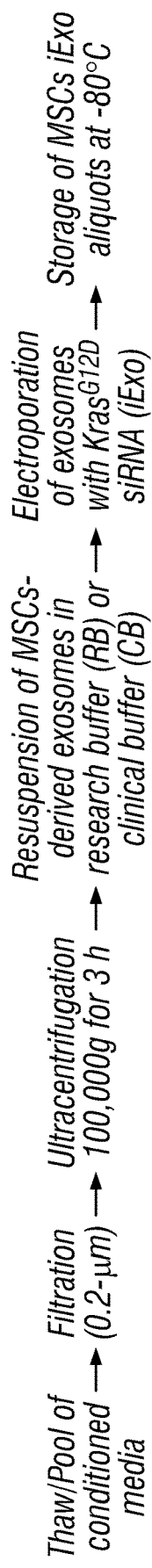
Figure 1D:
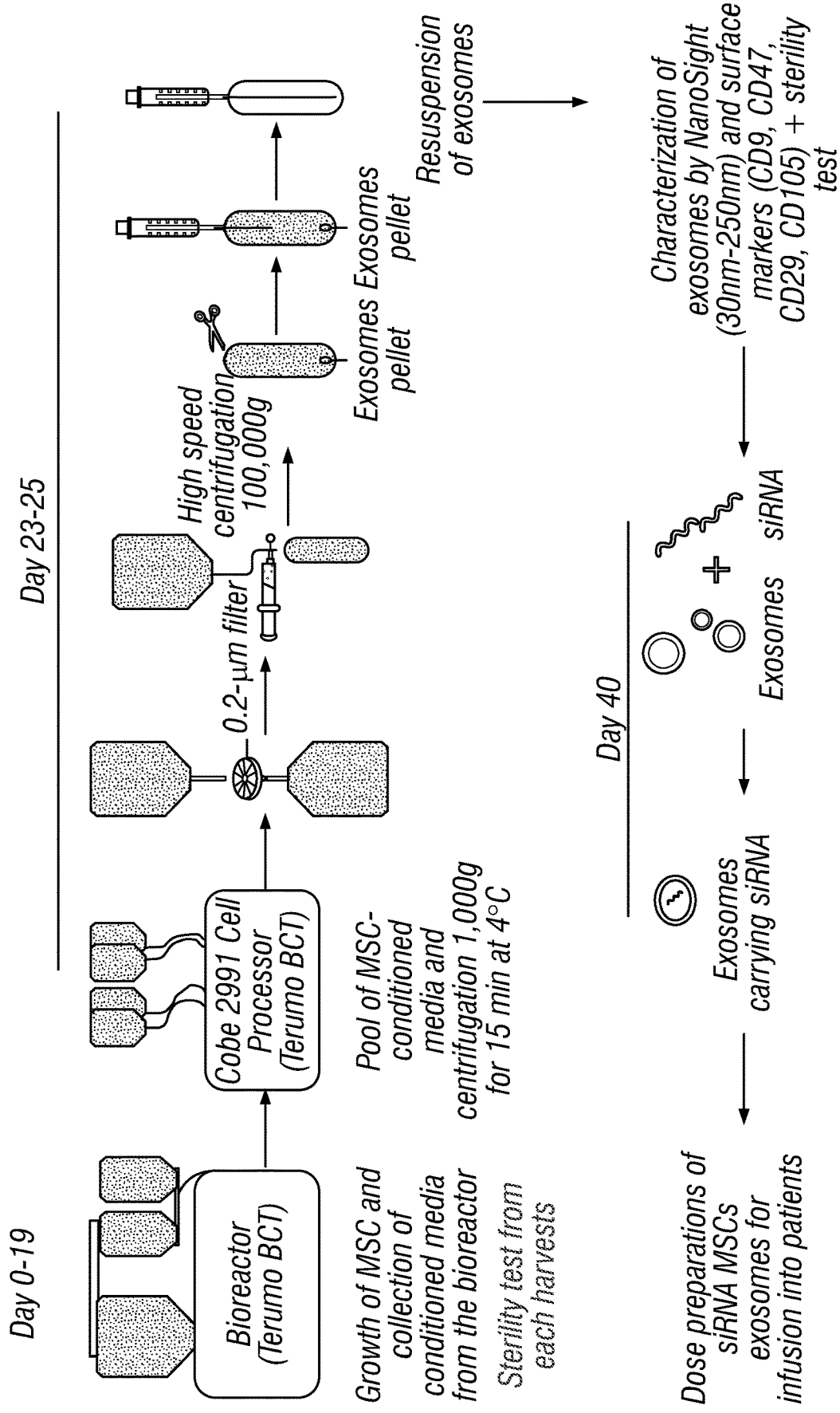
Figure 2:
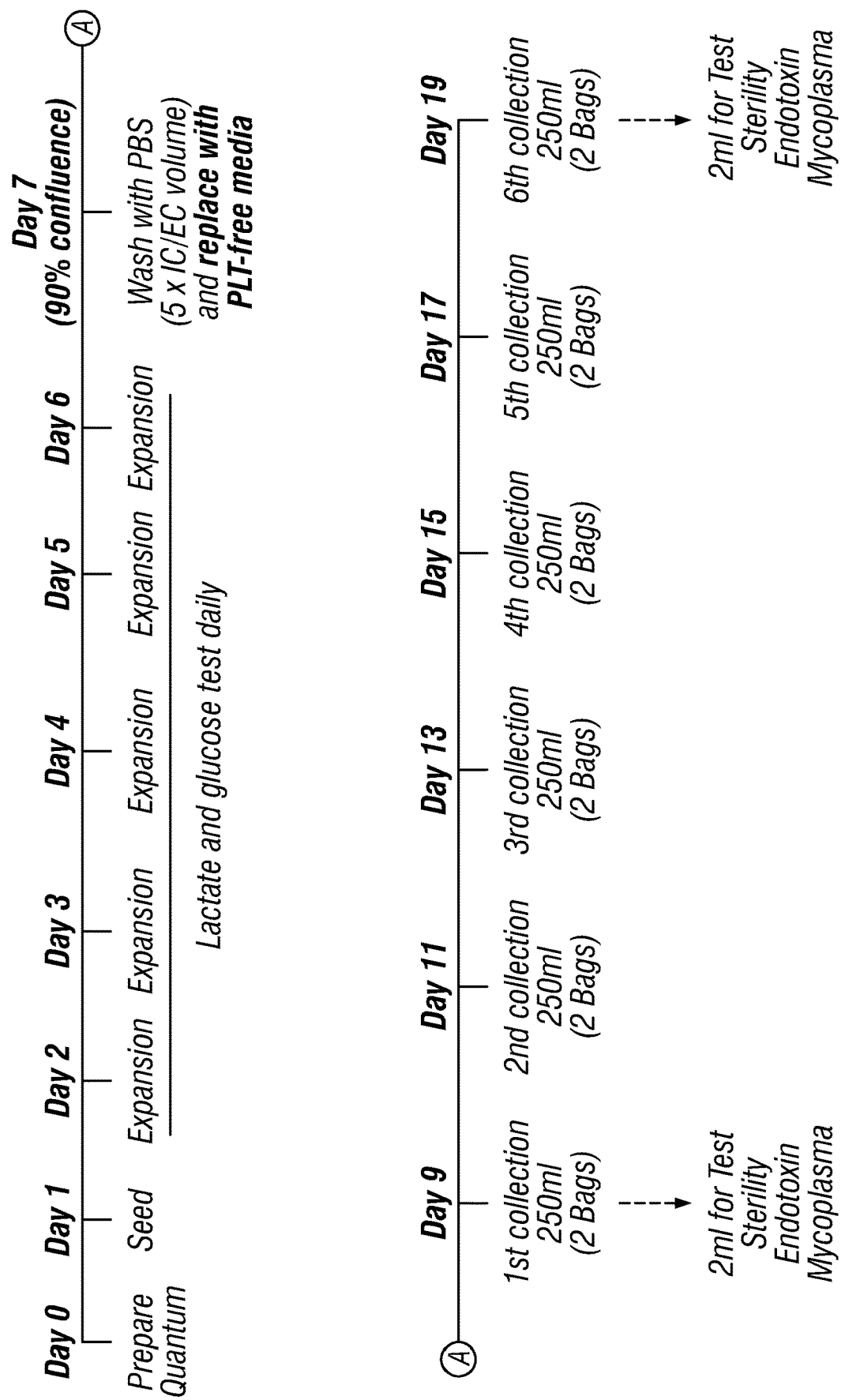
FIG. 2: Schematic representation of the strategy for the production of conditioned media containing EVs from MSCs cultured on a bioreactor.

A unique step in the present strategy which has not been reported by others, involves the initial use of the platelet lysate for optimal MSC confluence in the bioreactor followed by the next step where once the MSCs in the bioreactor reach 85% or greater confluence the growth media is exchanged for serum-free conditioned media. This step avoids contaminating the ultimate product with the exosomes that are found in large quantities in platelet lysate and would otherwise dilute the MSC-derived exosomes. The conditioned medium was left in the bioreactor for 48 hours and then collected for EVs purification (FIG. 1). The bioreactor continually produced EVs for 12 days which included 6 collections (one every 48 hours) (FIG. 2).

Figure 3:
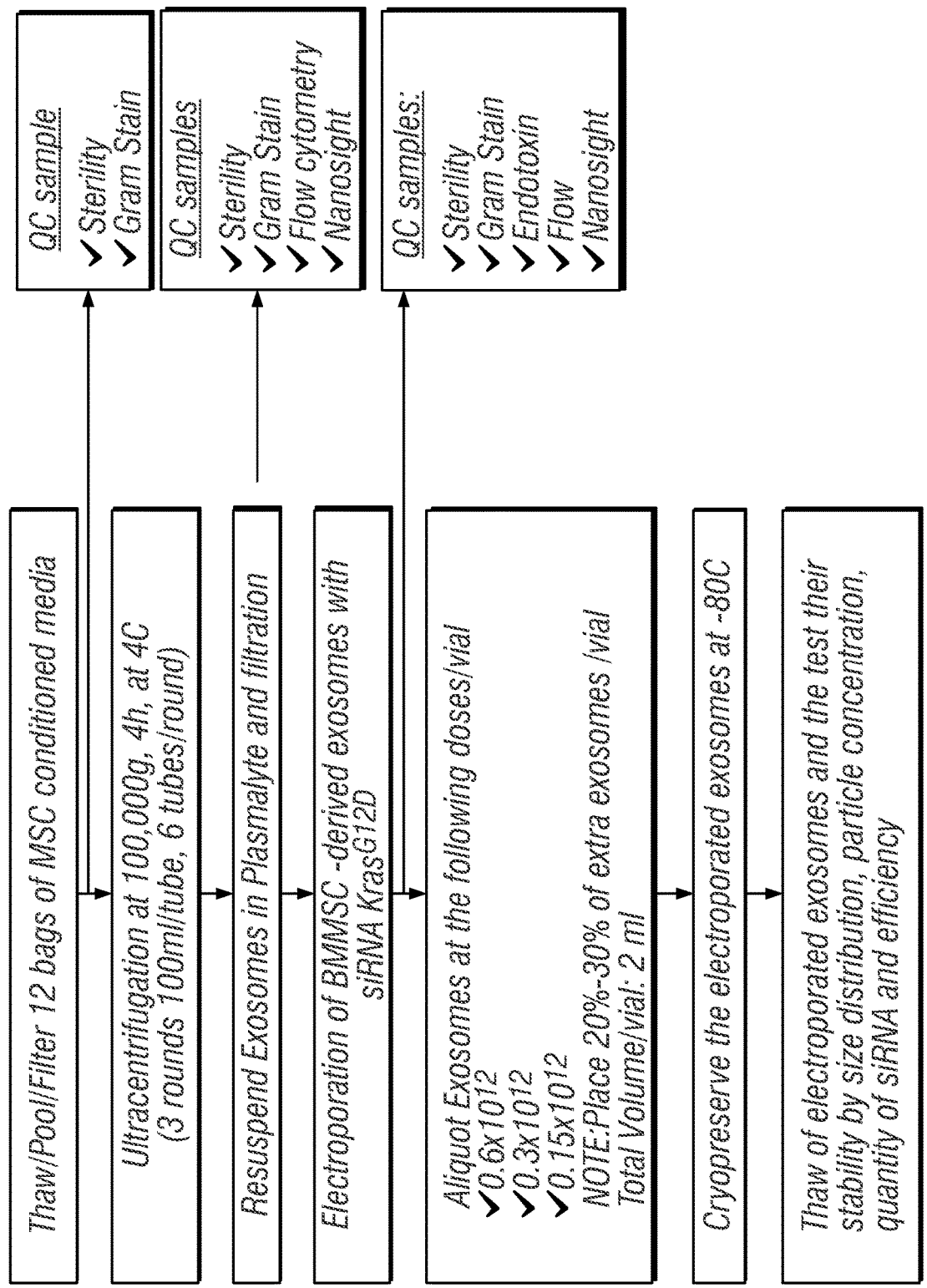
FIG. 3: Schematic representation of the strategy for the isolation of EVs from MSC-conditioned media cultured on a bioreactor.
Figure 4A:
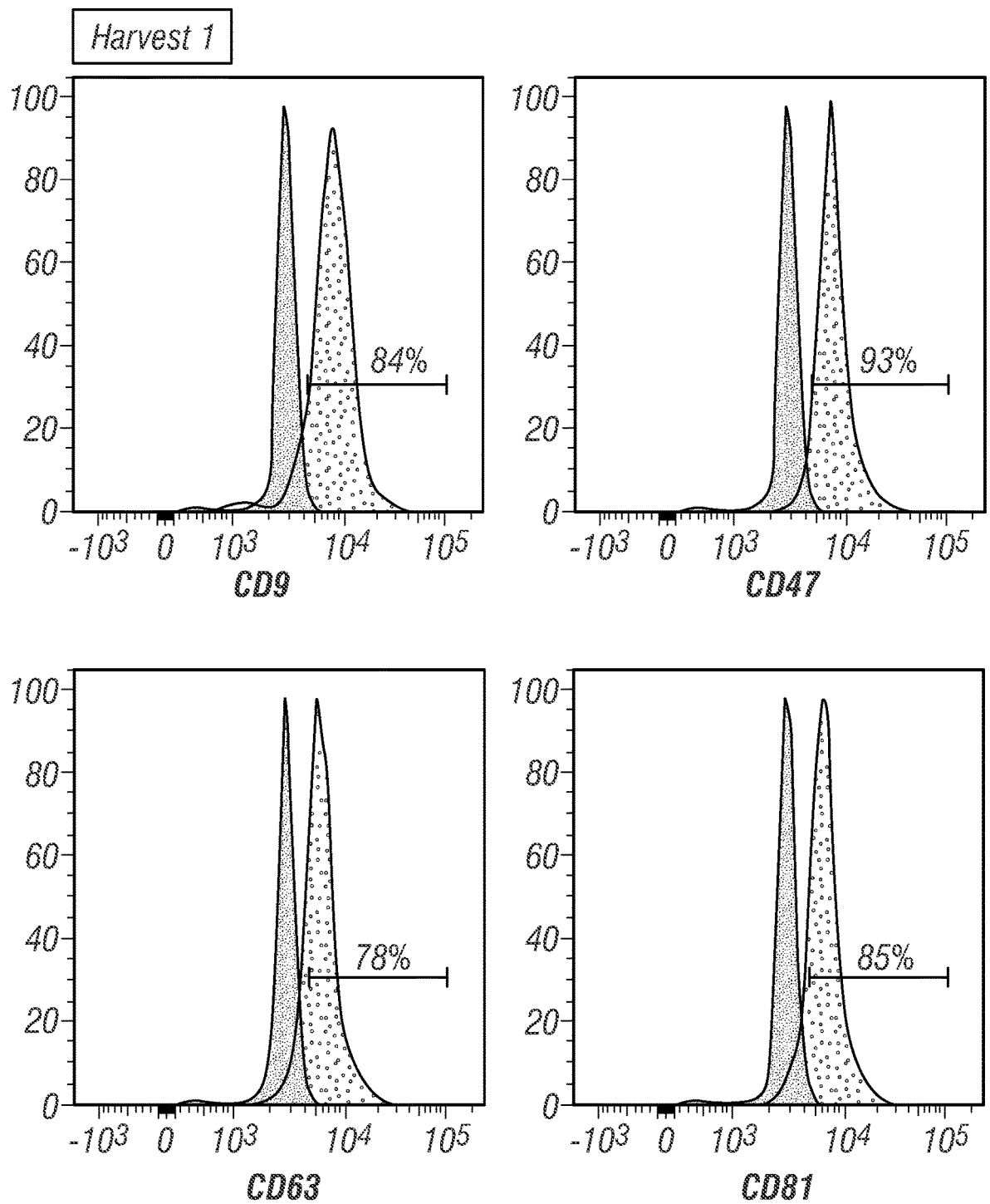
FIGS. 4A-4B: Identification of MSC-derived exosomes produced in the bioreactor.
Figure 4A:
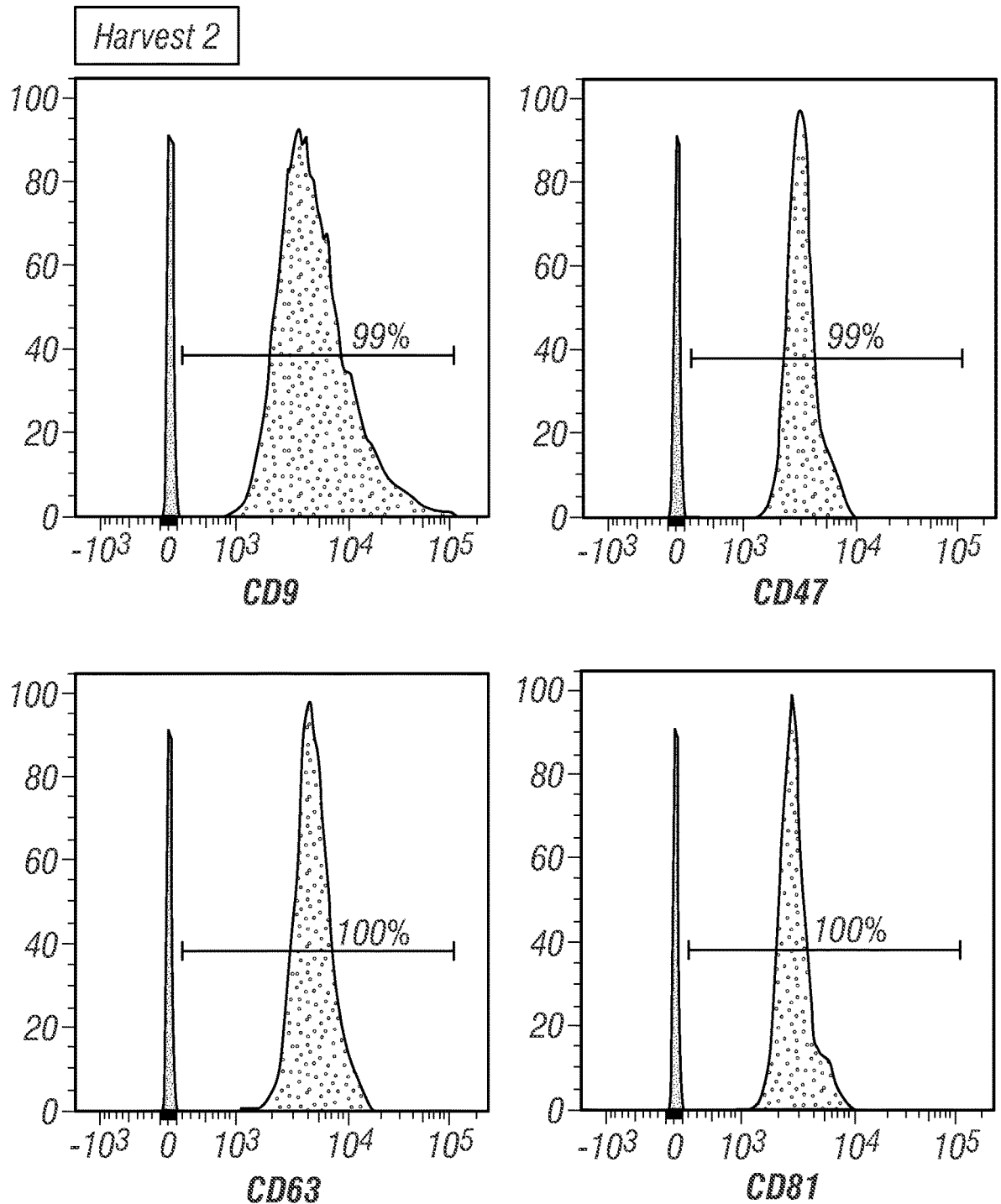
Figure 4A:
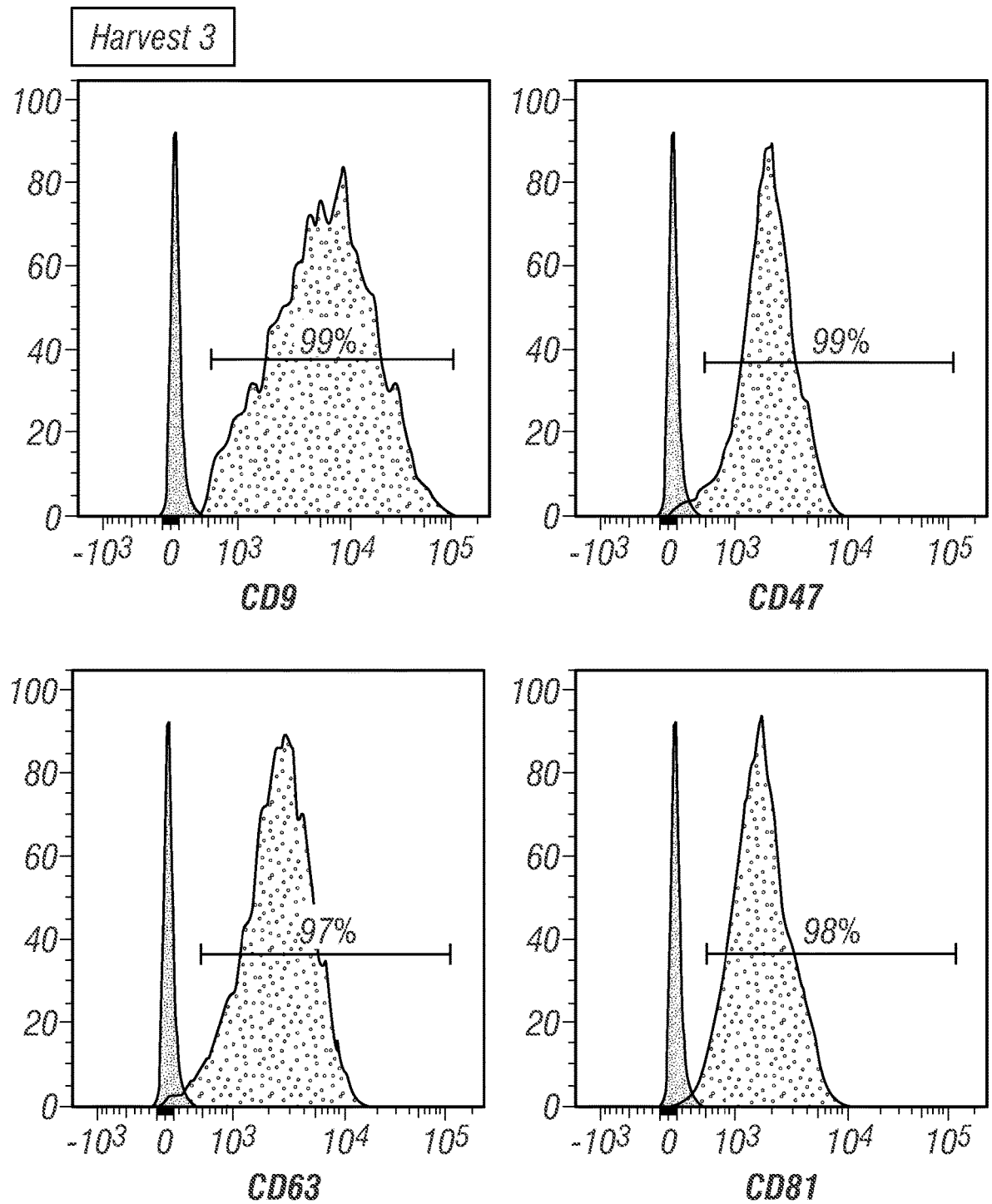
Figure 4A:
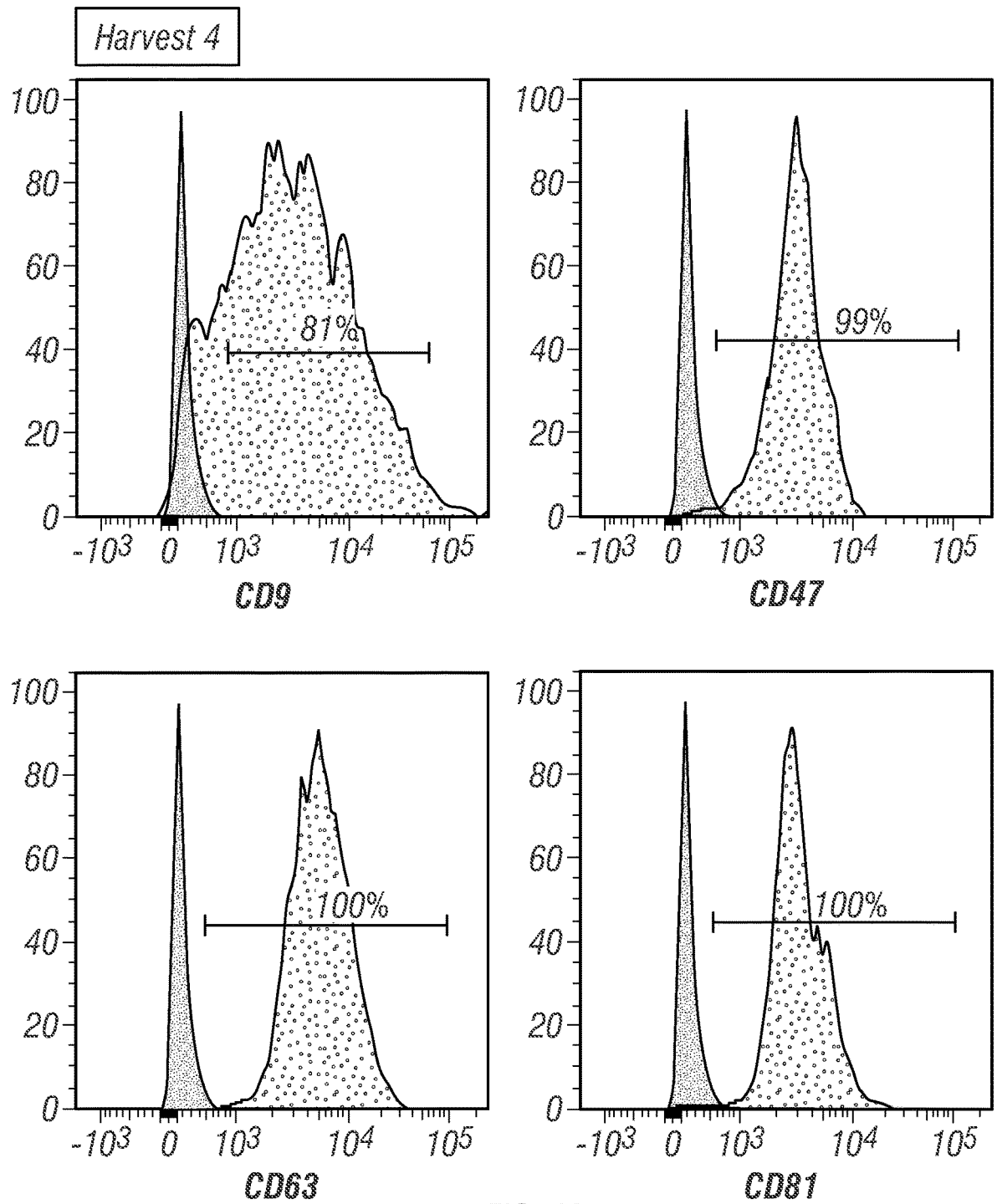
Figure 4A:
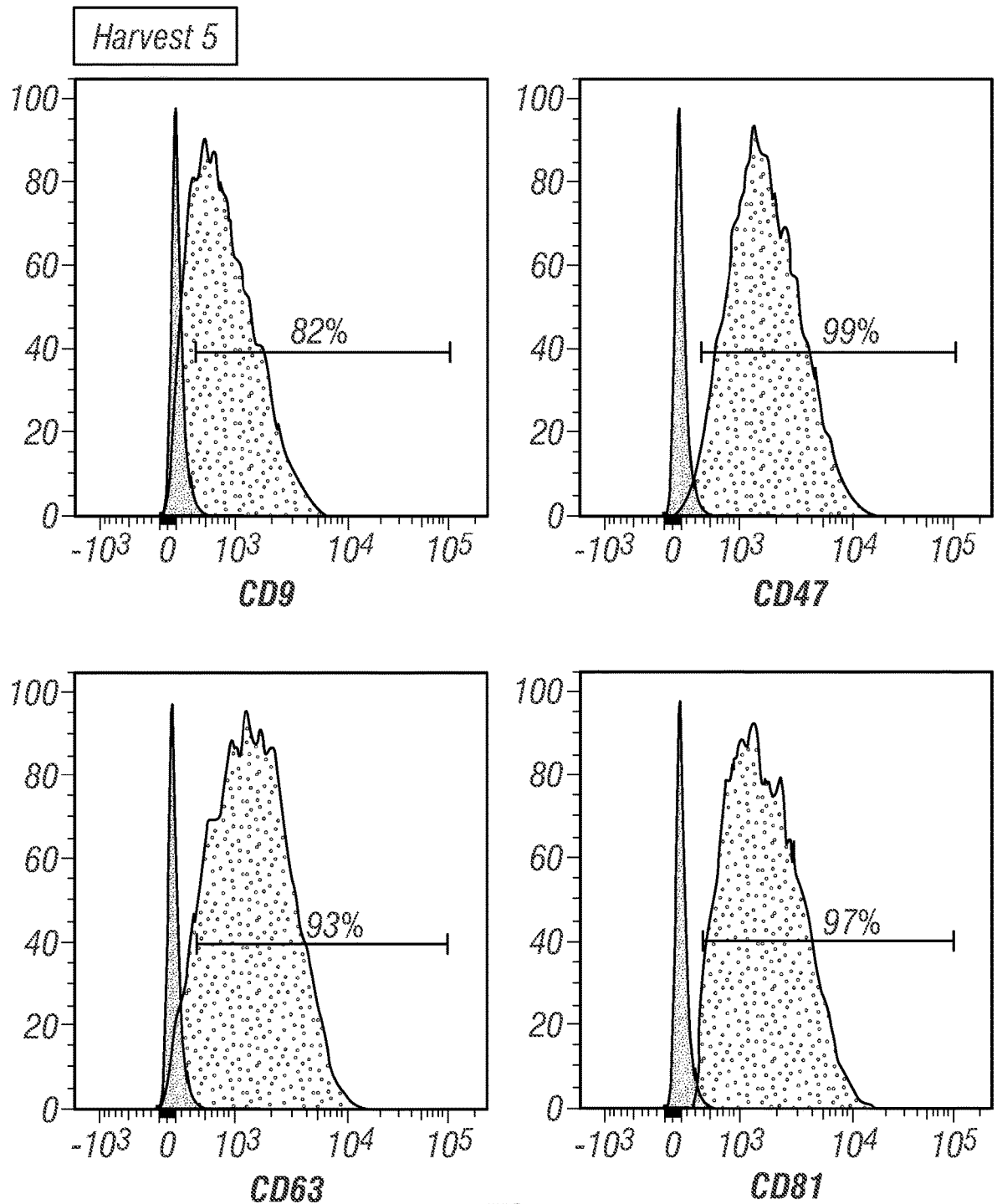
Figure 4A:
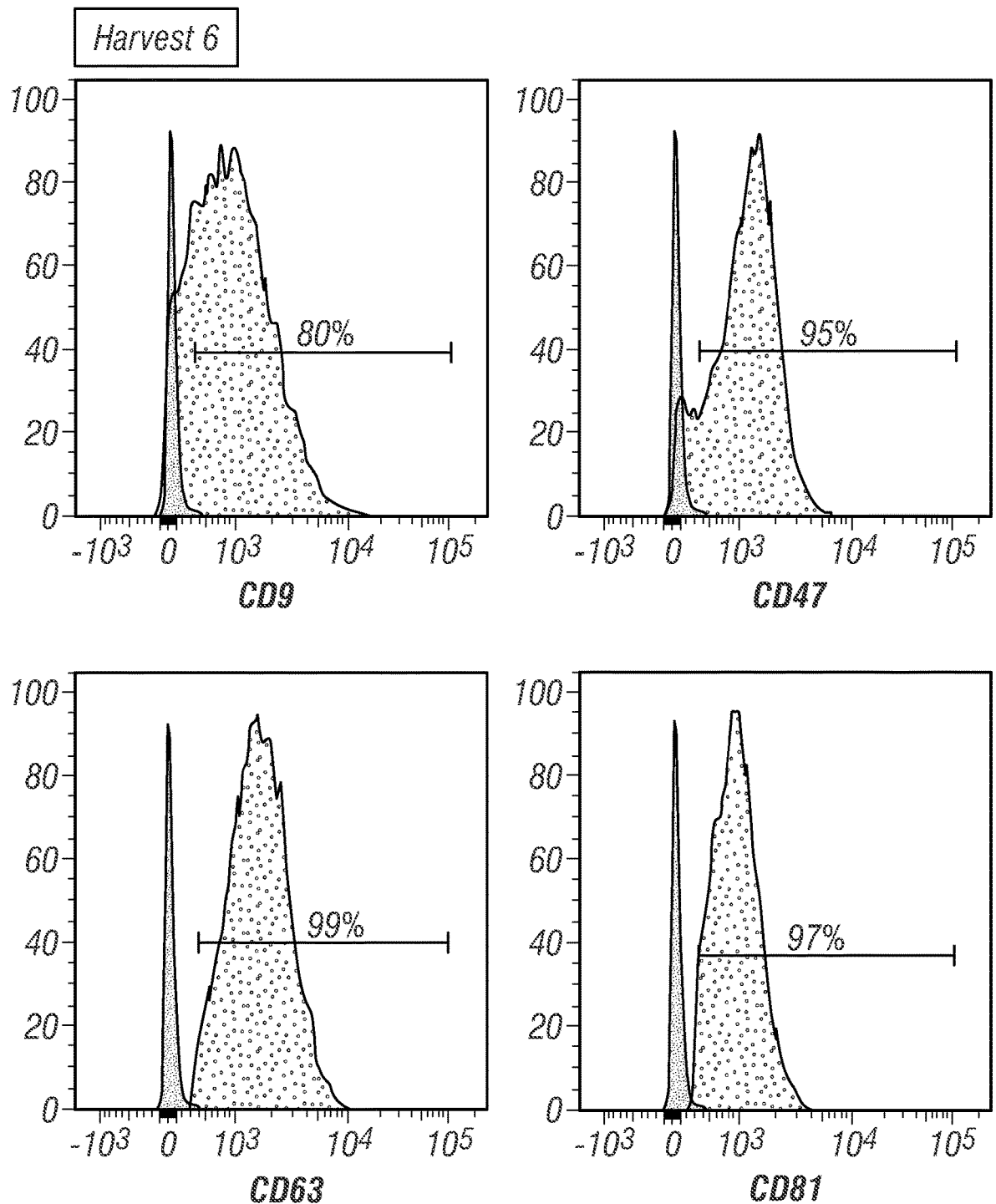
Figure 4B:
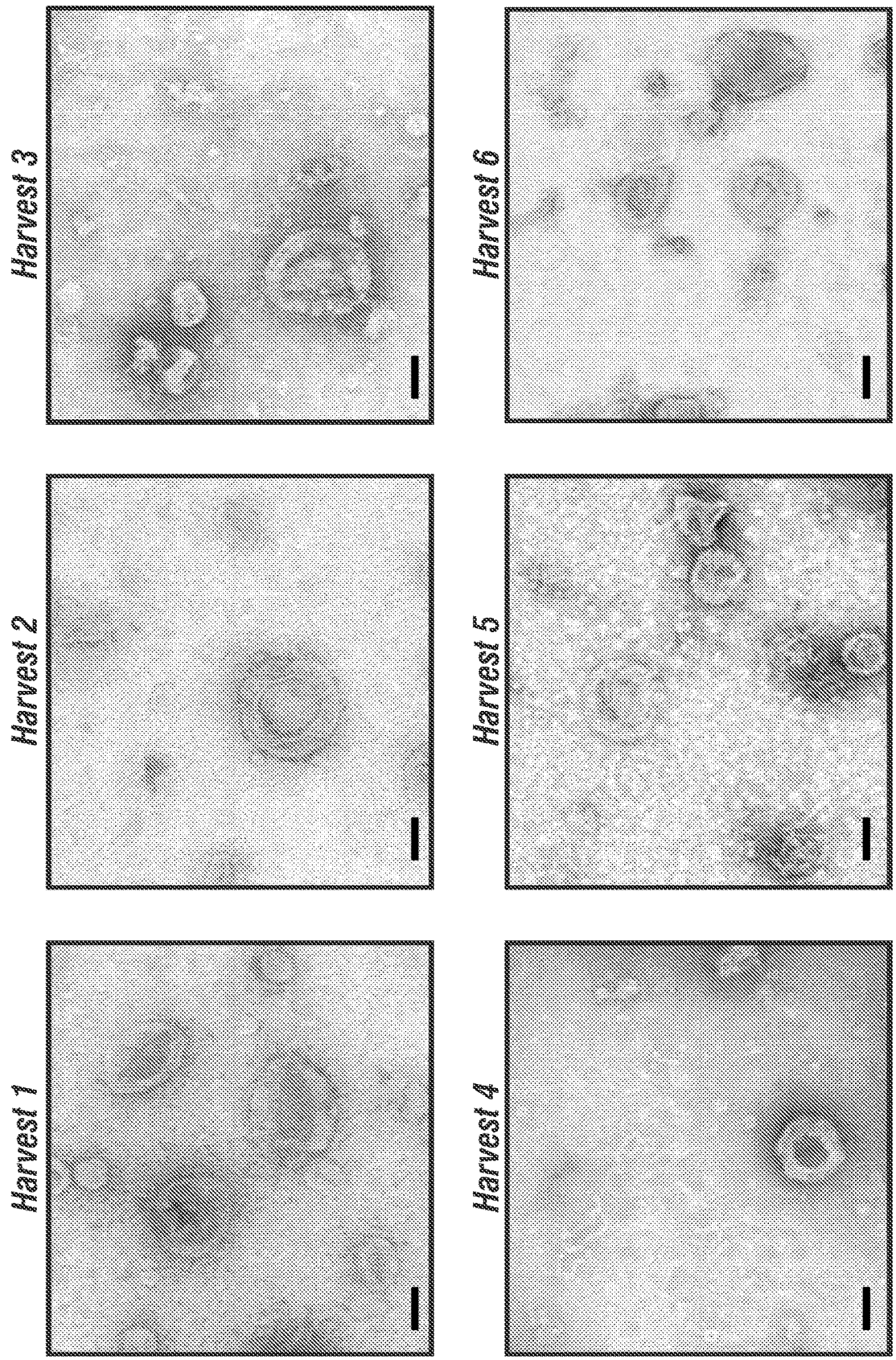

Using this approach, the system was optimized by sequentially collecting EVs from approximately 600 million MSCs. After 21 days, the conditioned media fractions, which were collected every 48 hours and stored at −80° C., were thawed, pooled and filtered in a functionally-closed system (FIG. 3).

A pump (Baxter) was used for the filtering following heat-sealing of the bag tubing for this process, consistent with the GMP-compliance needed for clinical cell therapy procedures. The EVs were isolated from the conditioned media as exosomes by ultracentrifugation at 100,000 g for 4 hours at 4 C, using the XE-90 Ultracentrifuge (Beckman Coulter). The Baxter pump and heat-sealed tubing were used to remove the exosomes from the ultracentrifuge in a functionally-closed manner for the highest quality clinical product.

Exosomes were enriched by filtration and ultracentrifugation and exosome numbers ranged between 900 billion to 4500 billion per harvest. The total number of exosomes generated ranges between 9.8 and 15.1 trillions per bioreactor run. The mode size of exosomes from all 6 harvests of a bioreactor run showed a characteristic peak at about 170 nm. The measures of exosomal protein content approximated the exosome counts as determined by Nanosight analyses. Notably, the metabolic harvests of conditioned media remained constant, supporting that the MSCs remained viable.

Figures 5A, 5B:
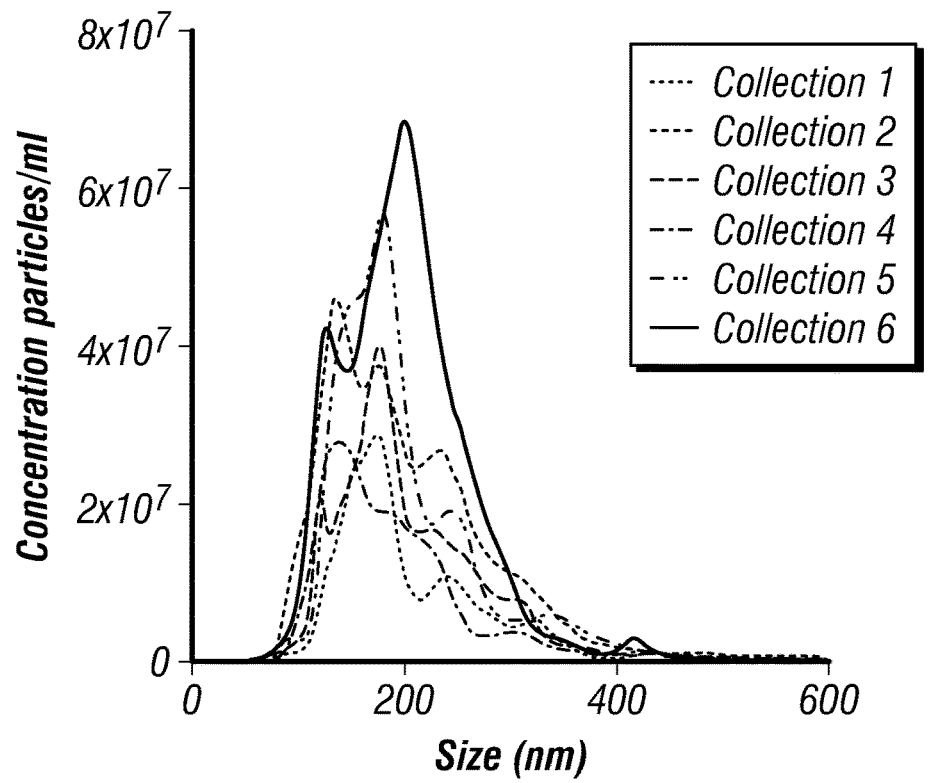
Figure 5E:
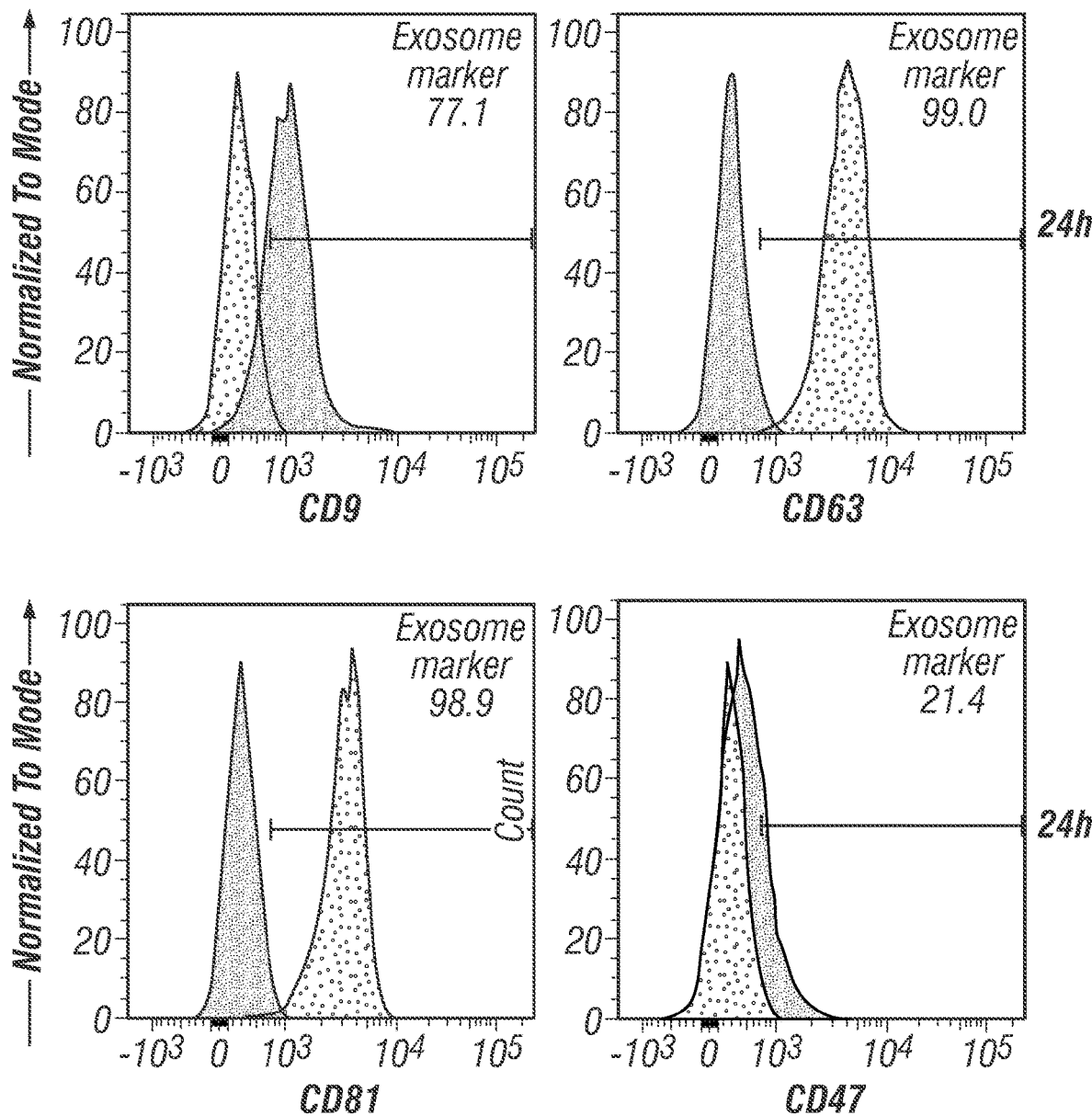
Figure 5E:
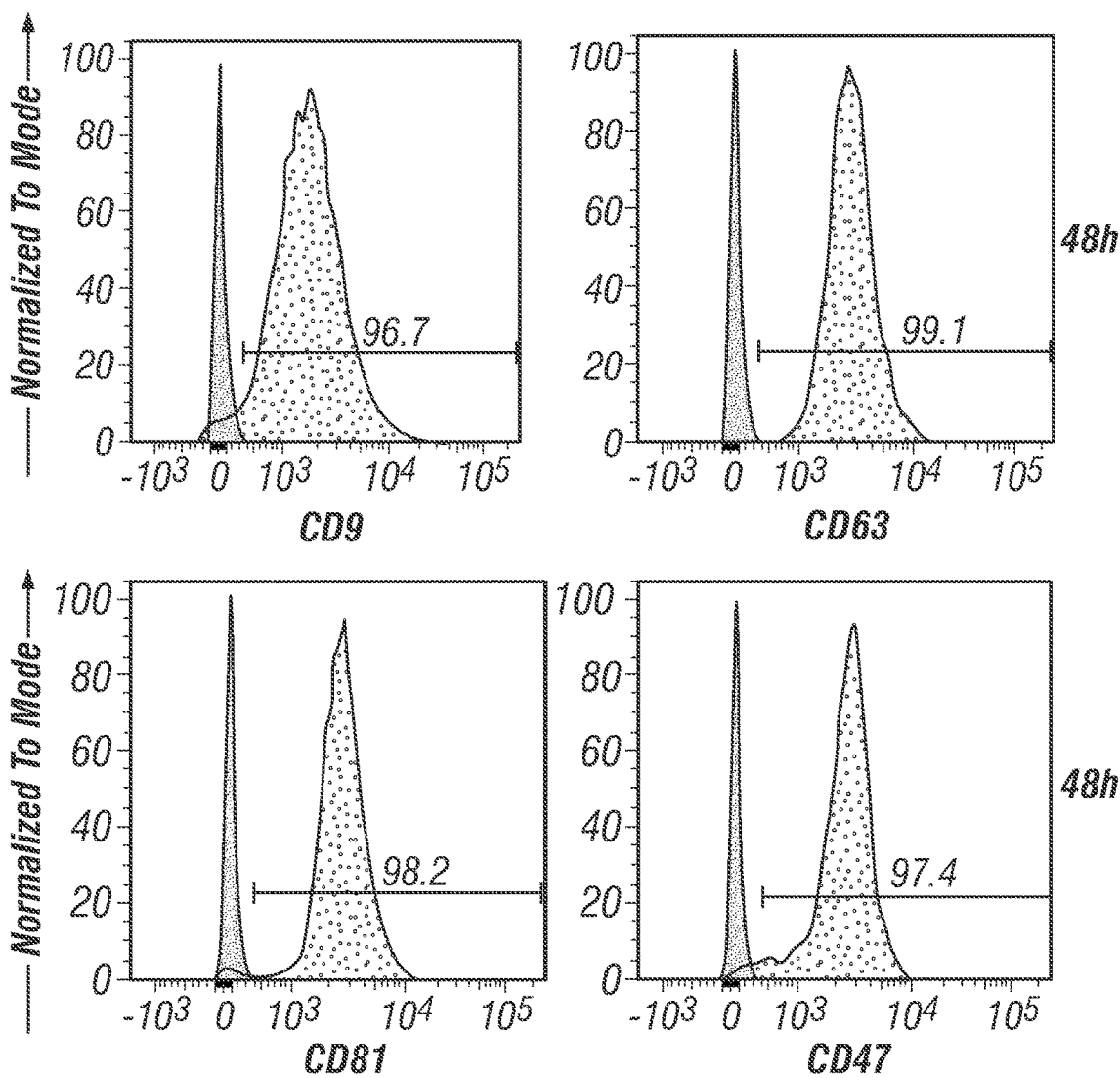

The purified exosomes were identified by the flow cytometric expression of the exosome surfaces markers: CD63, CD47, CD9 and CD81; and Transmission electron microscopy (TEM) (FIG. 4). Additionally, nanoparticle tracking analysis and microBCA assay were used to quantitate the exosomes (FIG. 5). The yield from one bioreactor run was a minimum of $10 \times 10^{12}$ exosomes, which is equivalent to the approximate exosome yield from 100 T-225 flasks. Thus, the present method allows for efficient, clinical grade production of exosomes.

Example 2—Electroporation of Exosomes

Figure 7:
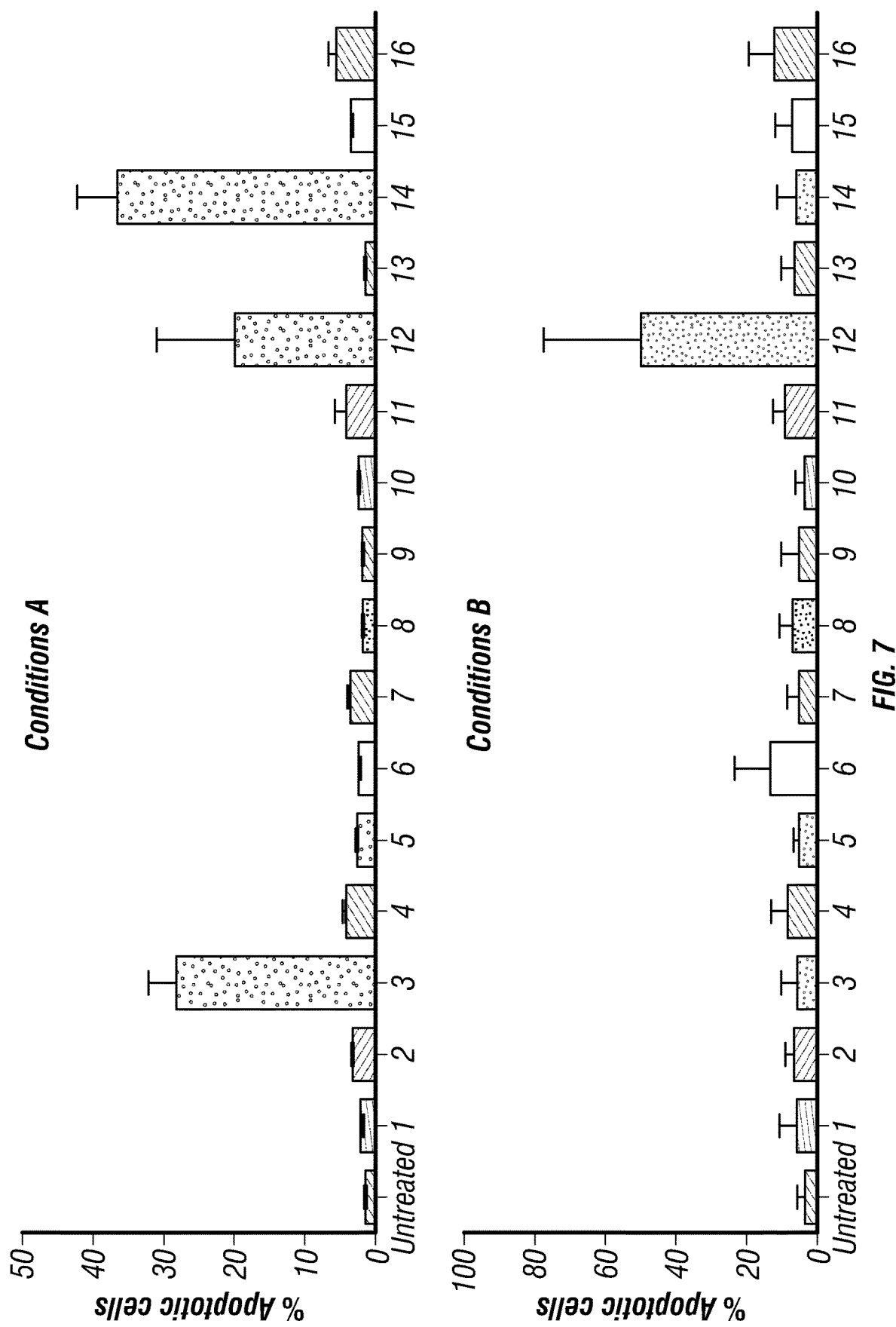
FIG. 7: Evaluation of MSC-derived exosomes electroporation using sixteen different nucleofactor programs and three different nucleofactor solutions. Efficiency of electroporation was evaluated by the apoptosis induced by siRNA delivery by MSC-derived exosomes on recipient cells after 48 hours.
Figure 7:
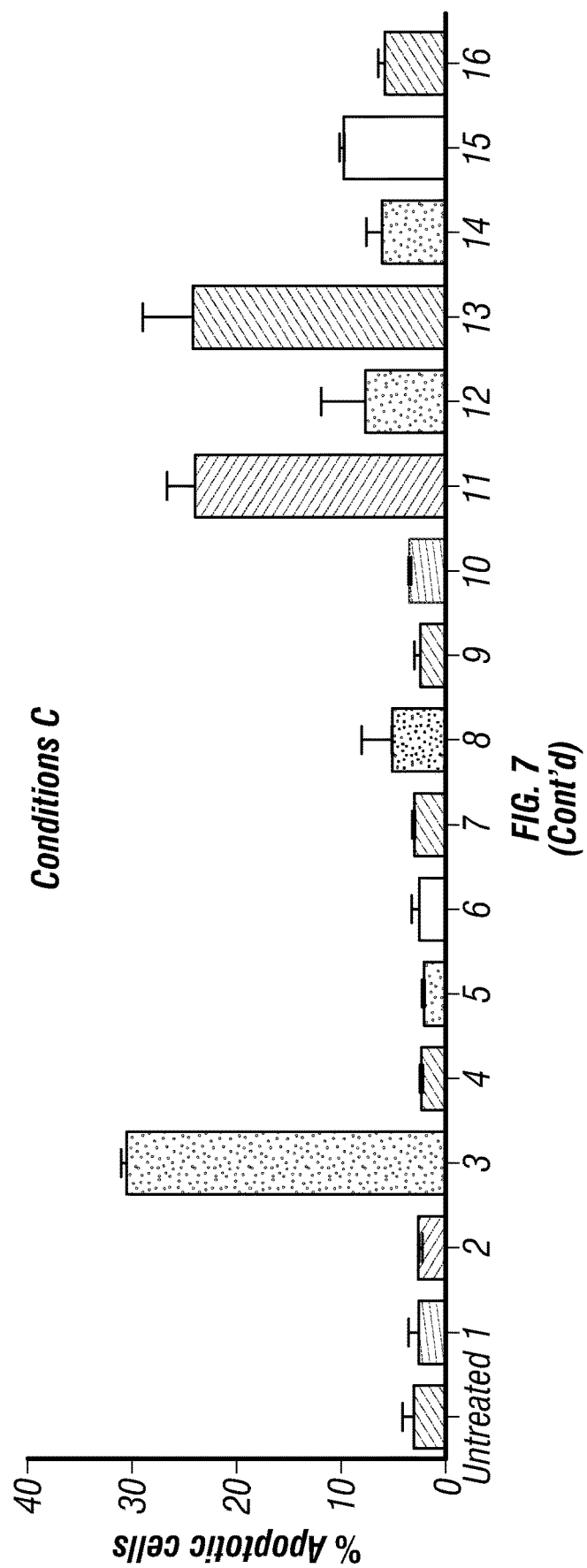

The 4D Nucleofactor system was adapted with LV Unit to allow for closed, efficient, and scalable in vitro transfection of large exosome numbers in the range of $2.5 \times 10^{10}$ to $2.5 \times 10^{12}$ exosomes, such as the exosomes derived in Example 1. The 4D Nucleofactor device contains three different Nucleofector Solutions, SE, SF, and SG, each of which were tested in combination with sixteen different Nucleofector Programs using MSC-derived exosomes and specific siRNA. The efficiency of each condition to efficiently incorporate the siRNA into MSC-derived exosomes was evaluated by apoptosis assay of recipient cells induced by MSC-exosomes carrying siRNA (FIG. 7).

Figure 8A:
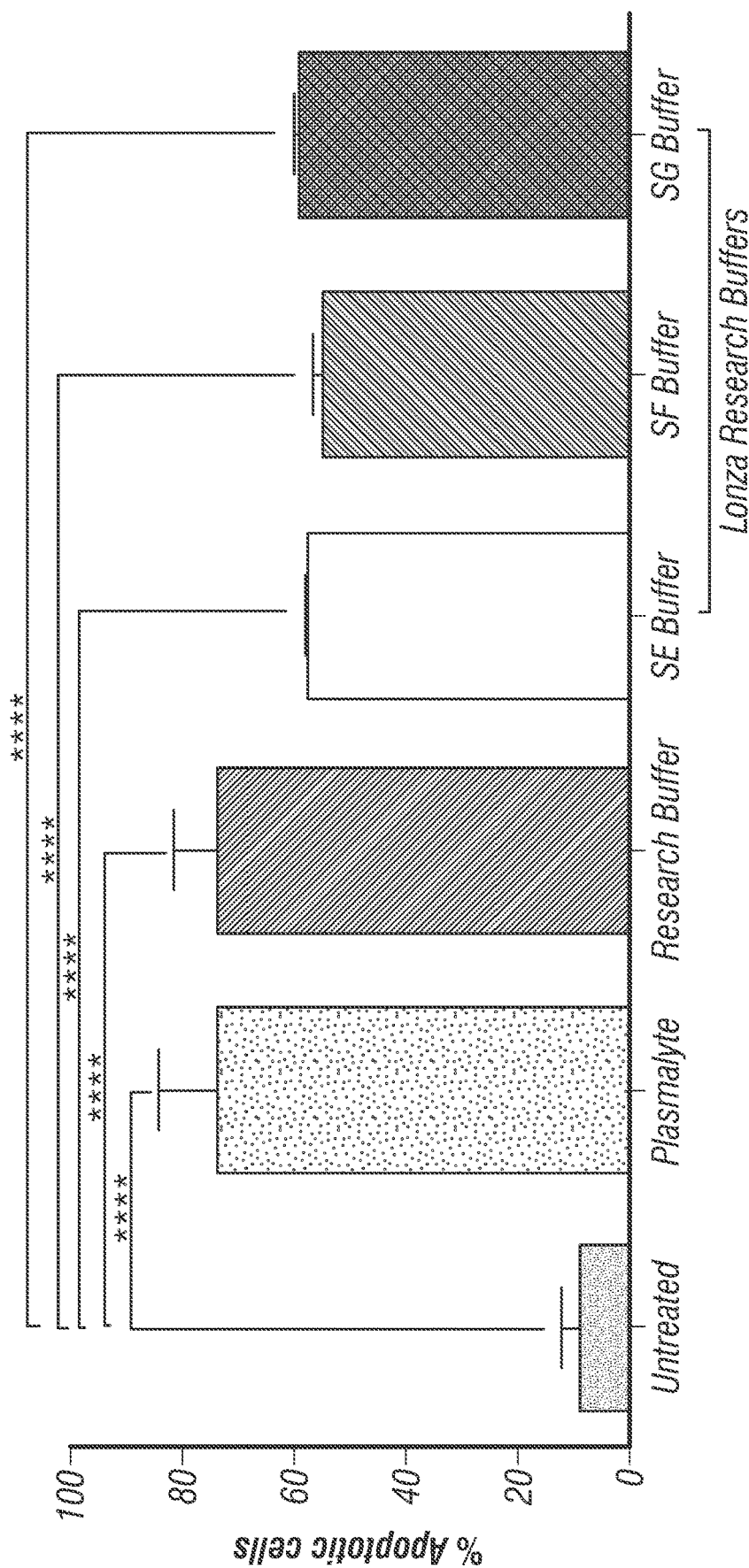
FIGS. 8A-8C: Evaluation of MSC-derived exosomes electroporation using five different solutions.
Figure 8B:
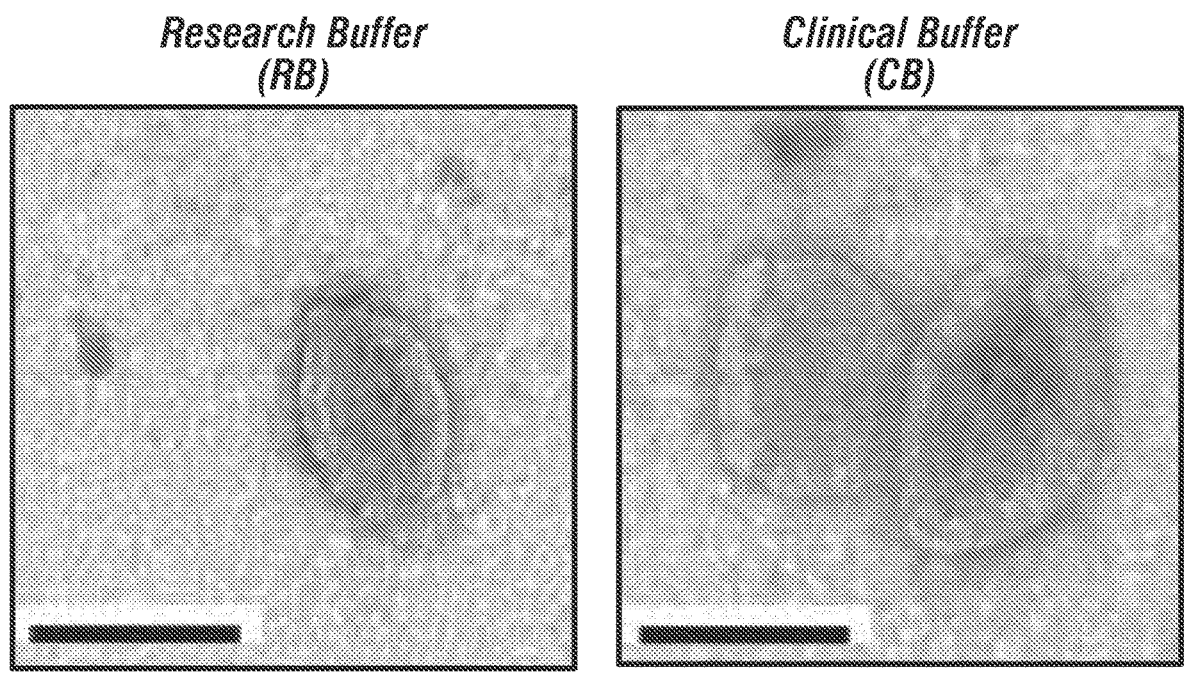

Previously, a defined electroporation buffer (research buffer, 'RB') was used to introduce siRNA into exosomes, which necessitated a wash step of the exosomes prior to treating cells or mice as that buffer is not approved for human use. The wash step was associated with a loss of exosomes, which could be alleviated by the use of a diluent that enabled successful electroporation of the siRNA into exosomes and that could be directly administered to cells or mice. A clinical buffer (PLASMALYTE-A®, 'CB'), an FDA-approved diluent for human use, which is used for MSCs and many other cellular product infusions into patients, was tested for electroporation. Following electroporation of MSC-derived exosomes, electron microscopy analyses confirmed the presence of intact exosomes using either the originally formulated research buffer (RB) or PLASMALYTE-A® (FIG. 8B).

Example 3—Optimization of Conditions in Exosome Manufacture

To determine the best time to produce exosomes from MSCs cultures, the collections of conditioned media were performed at different times (FIG. 5D). Data obtained from nanosight (i.e., number of particles) were combined with the data obtained for flow cytometry (i.e., percentage of exosome markers). The results showed that the number of particles from MSCs reached the highest level at 24 hours and is maintained until 48 hours. After that time the number of particles decreased significantly. The flow data indicated that the percentage of exosomes marker were enriched at 48 hours as compared to the percentage at 24 hours (FIG. 5E). As the number of particles between 24 hours and 48 hours was not significantly different, the 48 hour time point was selected as the time point for collection.

Figure 6A:
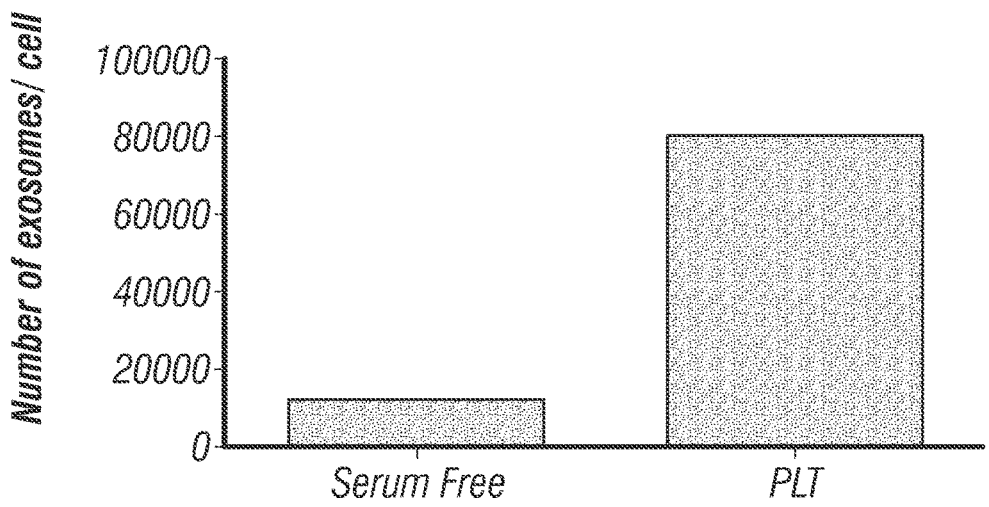
FIGS. 6A-6B: Quantification of MSC-derived exosomes produced in media supplemented with human platelet lysate (hPLT) or serum-free condition.
Figure 6B:
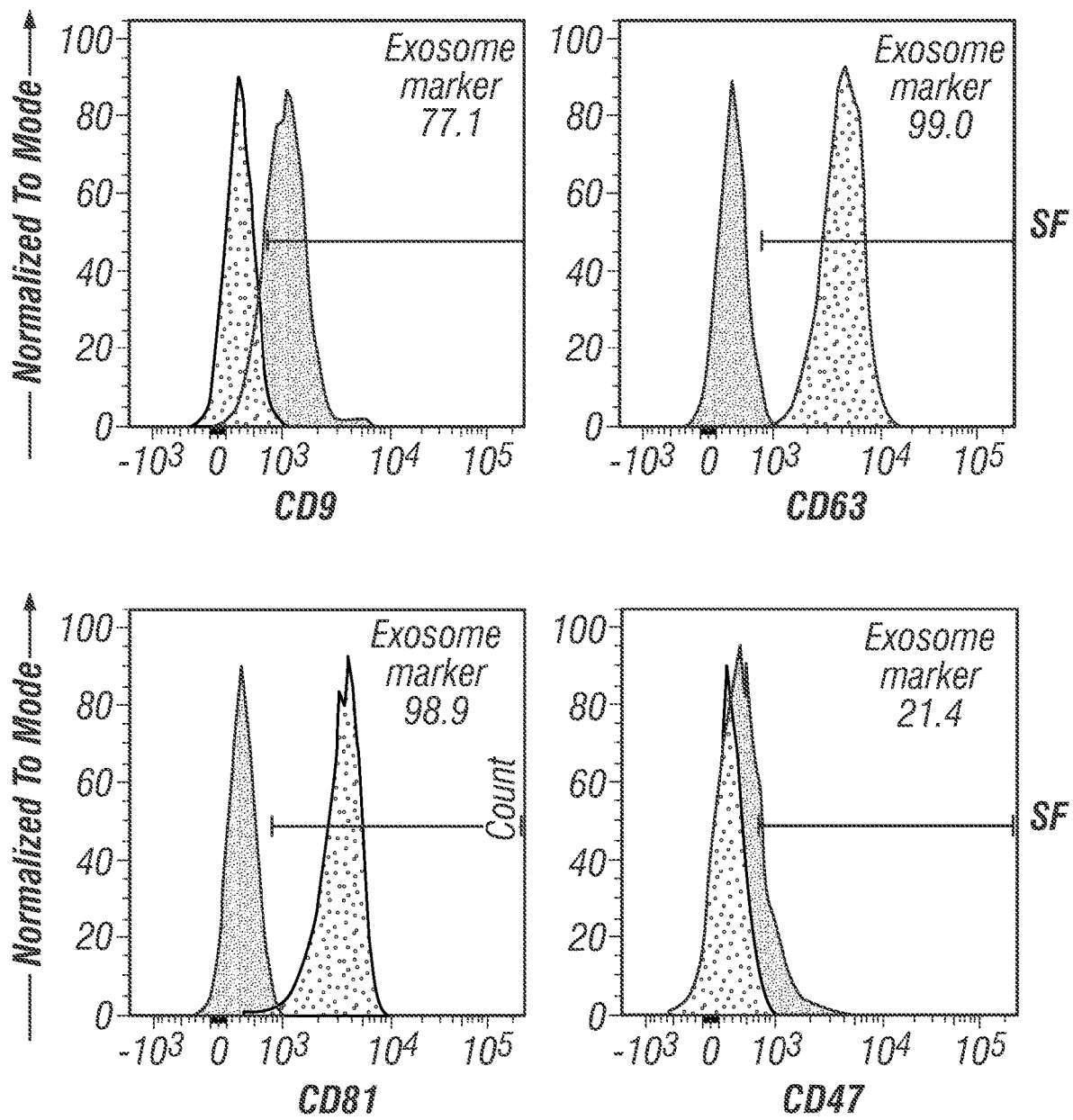
Figure 6B:
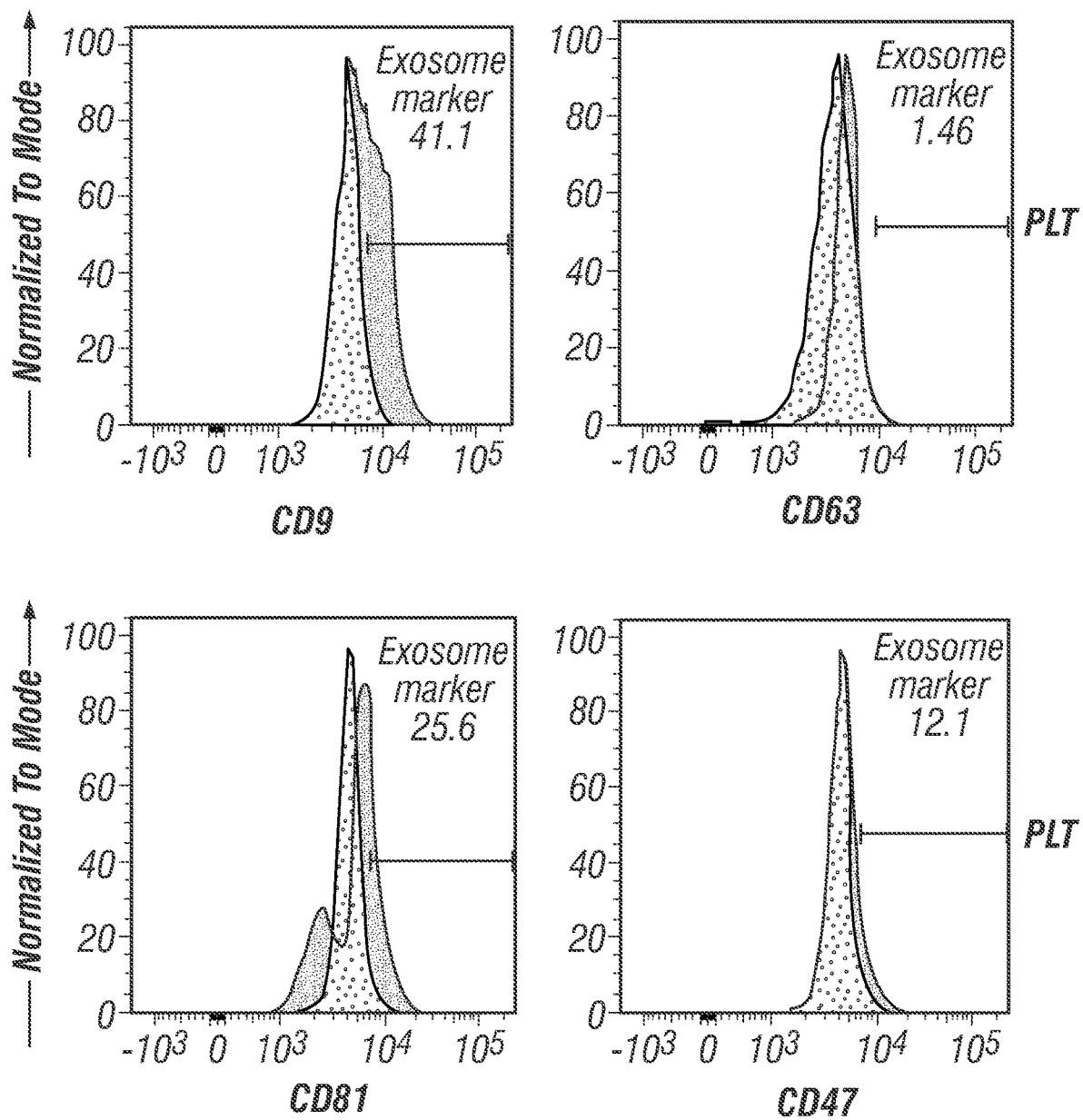

Next, to determine the ideal conditions to produce exosomes from MSCs in culture, MSCs-derived exosomes were isolated from conditioned media after 24 hours of culture with and without media containing PLT. Results showed that the number of particles isolated from media with PLT was higher than with serum-free media (FIG. 6A). However, the flow cytometry of exosome markers indicated that the percentage of exosomes was low, possibly due the high number of protein and lipids in PLT (FIG. 6B).

Figure 9:
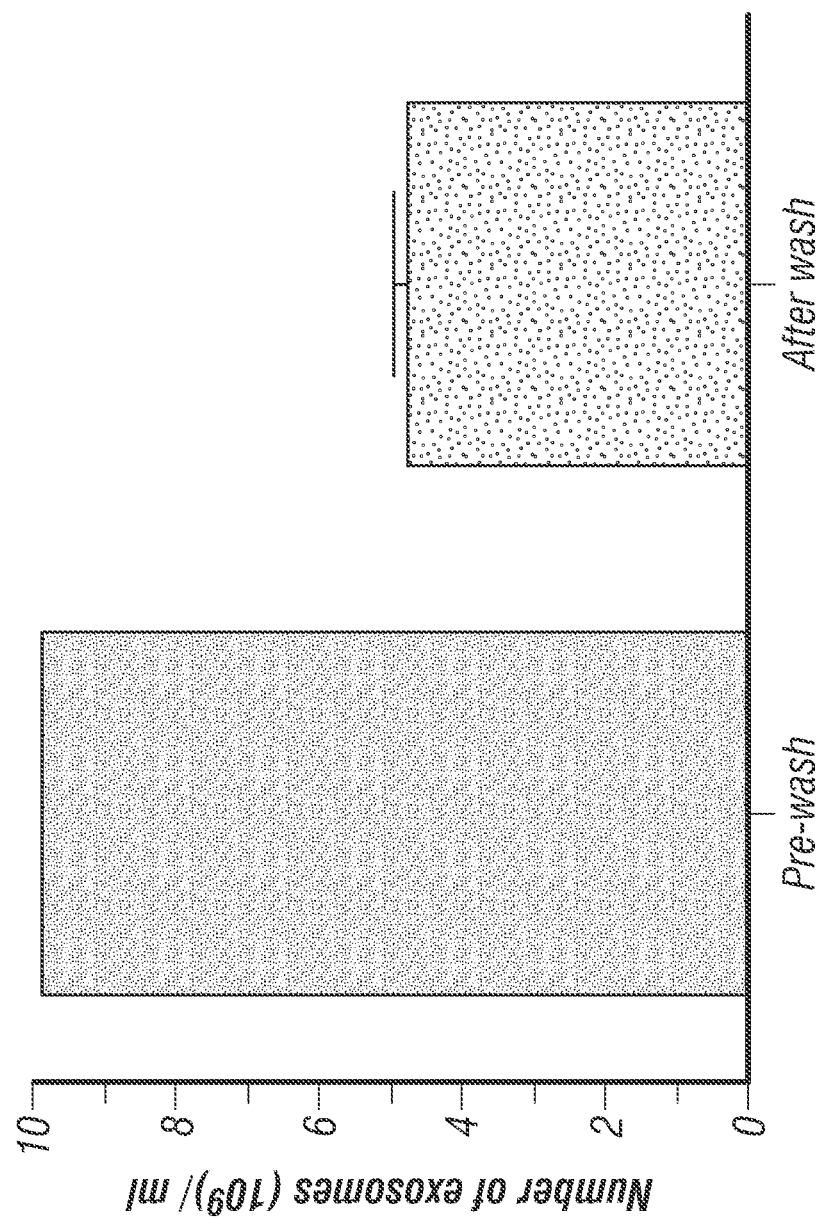
FIG. 9: Number of exosomes pre- and post-ultracentrifugation. Electroporation of exosomes using research buffers include a second wash step, which may lead in loss of at least 50% of the sample.
Figure 10A:
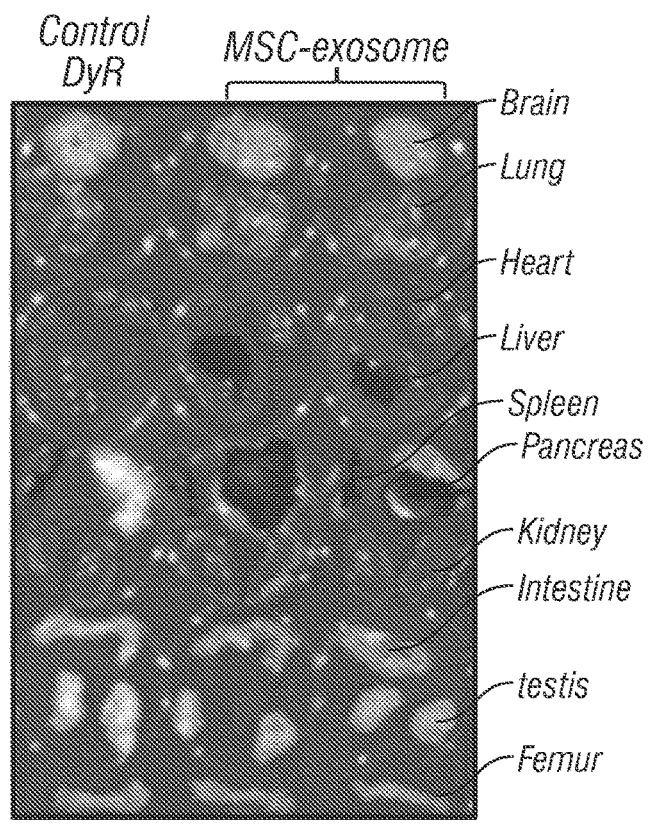
FIGS. 10A-10D: Biodistribution of pre-labeled MSC-derived exosomes produced in the bioreactor and injected into mice. Fluorescence of DIR-labeled MSC exosomes 6 hours after intraperitoneal (FIG. 10A, 10B) or intravenous (FIG. 10C, 10D) administration of $8 \times 10^9$ labeled exosomes in WT nude mice. (A, C) Dissected organs. (B, D) Dissected organs without spleen and liver.
Figure 10B:
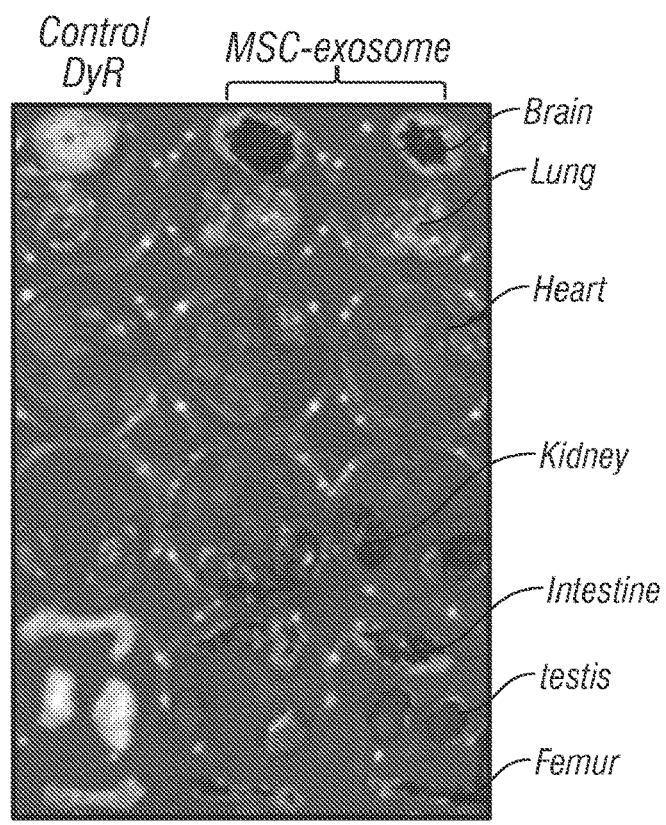
Figure 10C:
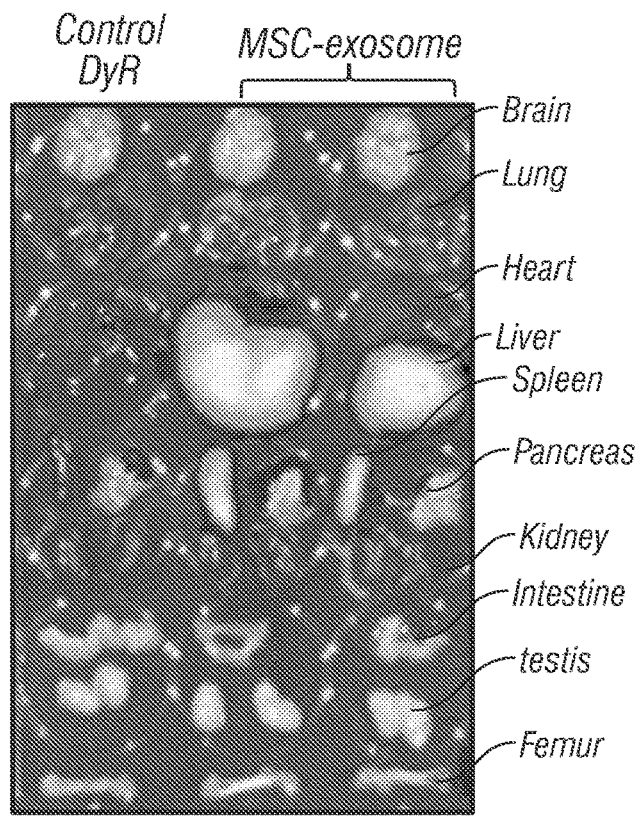
Figure 10D:
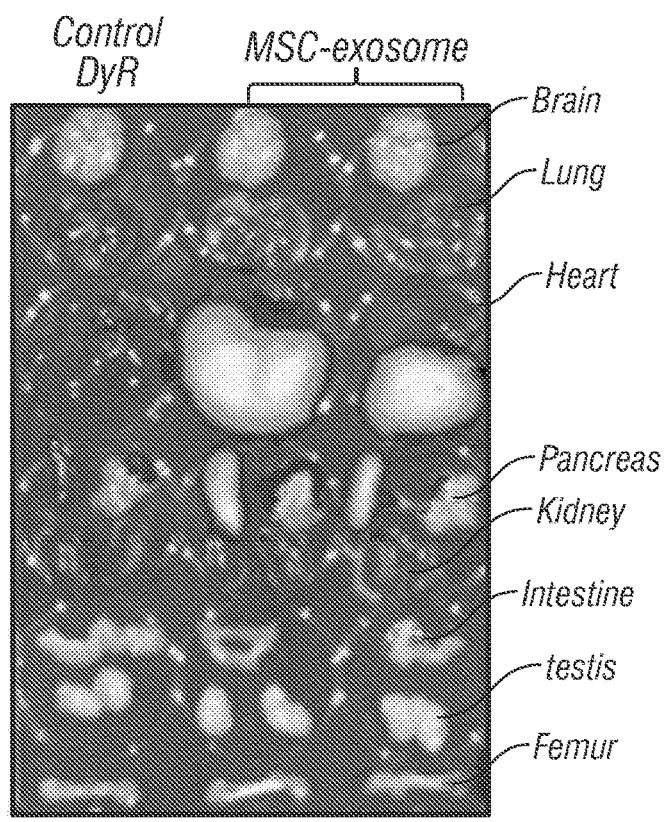

Thus, the process of electroporation of small sequences of nucleic acid or proteins into exosomes was optimized using a sterile solution (i.e., PLASMALYTE-A®) (FIG. 8A), which can be directly infused in humans, reducing the manipulation, loss of material, and the cost of the therapy (FIG. 9). Five different research buffers were tested before demonstrating that the PLASMALYTE-A® produced the optimal electroporation result (FIG. 8A). Furthermore, the ability of MSC-derived exosomes produced by this strategy to target several tissues was demonstrated in vivo (FIG. 10).

Figure 8C:
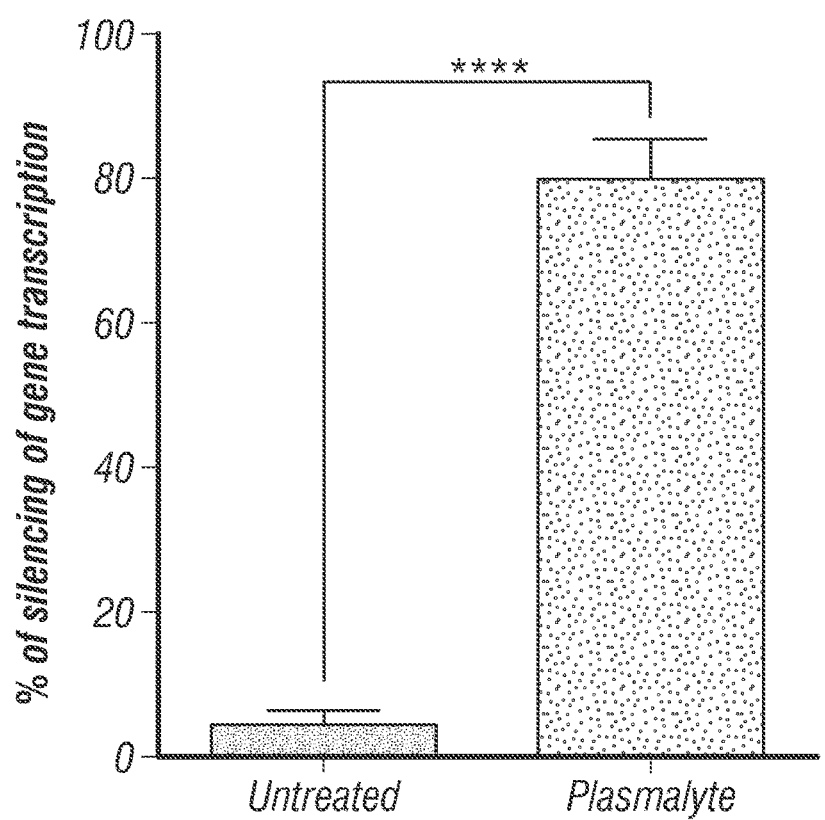

Thus, the present studies demonstrated the efficient large-scale production of MSC-exosomes carrying KRAS siRNA which can silence the in vitro expression of the target RNA in recipient cells (FIG. 8C). This approach produces larger numbers of EVs by more than one log compared to previous methods. Additionally, the present methods will allow the direct infusion of the manipulated exosomes without washing or other manipulation.

Example 4—Materials and Methods

Cells: Bone Marrow derived MSCs passage 3, obtained from the Cell Therapy Laboratory at MD Anderson Cancer Center, were cultured in alpha MEM supplemented with 1% L-glutamine, 5% human platelet lysate, and 1% penicillin streptomycin (complete media). MSCs from 3 distinct donors were evaluated and a single donor was subsequently chosen based on its high exosomes production yield. For in vitro transfection, 250,000 Panc-1 cells were seeded per well of 6-well plate overnight. Before exosomes treatment, the monolayer was washed with 1 ml of PBS twice, and then treated with exosomes in 1 ml of serum-free media (RPMI supplemented 1% penicillin-streptomycin) for the indicated time points as described for each assay.

The clinical buffer (PLASMALYTE-A® pH 7.4 or 'CB') is composed of 0.09 M Sodium Chloride, 0.23 M Sodium Gluconate; 0.27 M Sodium Acetate Trihydrate, 5 mM Potassium Chloride, 3 mM Magnesium Chloride. It contains no antimicrobial agents. The pH is adjusted to 7.4 with sodium hydroxide.

Clinical grade exosomes were generated strictly from MSCs cultured in the GMP facility in the Cell Therapy Laboratory at MD Anderson Cancer Center. The Quantum bioreactor culture system (Terumo BCT) was primed (automatized process) with 1 L of 1×PBS and coated with 5 mg of human fibronectin (BD Biosciences, Germany) diluted in 250 ml of 1×PBS for 24 h. Then, the bioreactor was washed with 500 ml of cultured in alpha MEM supplemented with 1% L-glutamine, 5% human platelet lysate, and 1% penicillin-streptomycin (complete media) and loaded with $20 \times 10^6$ MSCs (passage 3) diluted in 25 ml of complete media, and expanded for 9 days using complete media. Fresh complete media was added continuously to cells and the inlet rate was adjusted as defined by the daily glucose and lactate measurements. After 9 days, when the cells reached approximately 80% confluence (as ascertained by glucose and lactose measurements), the cells were washed with 2 L of 1×PBS to replace the complete media with PLT-free media (alpha MEM supplemented with 1% L-glutamine and 1% penicillin-streptomycin). Bioreactor conditioned medium (250 ml) was then collected every 48 h in a sealed bag (closed system) for a total of 6 collections (harvests). During these 12 days, the culture did not expand based upon the constant glucose levels measured daily. Exosomes were thus continuously harvested every 48 h over 12 days. Harvests were stored at −80° C. for further processing. Each harvest was tested for sterility (confirmed negative for anaerobic and aerobic bacteria), endotoxin (<1 EU/ml) and mycoplasma (PCR, negative). The collections were then thawed overnight at 4° C., pooled, and centrifuged at 1,000 g for 15 min in a closed-system using Cobe 2991 Cell Processor (Terumo BCT). After removing large cell debris by centrifugation (1,000 g for 15 min at 4° C.), the conditioned media was filtered in a closed system using a filtering bag of 0.2-μm filters (Terumo BCT). Then, 600 ml of supernatant was transferred to six clear polycarbonate tubes (each tube has a 100 ml capacity) in a semi-closed system using a syringe and a line connected directly with the polycarbonate tube (Beckman Coulter), sealed and centrifuged for 3 h at 100,000 g in a type 45 Ti rotor (Beckman-Coulter). This process was repeated three times until all of the collections were spun (total of 1500 ml). The supernatant was then aspirated using a 16G syringe (BD Biosciences, catalog no. 14-826-18B) connected to a pump. The exosomes pellet was resuspended manually using a 18G syringe (BD, catalog no. 408360) in 4 ml (per tube) of clinical buffer and transferred to sterile glass container (APP Pharma, capacity of 30 ml). This was maintained at 4° C. for up to 72 h until all the centrifugations were completed. When all centrifugations were completed, the final pooled volume of resuspended exosomes was 72 ml. Pooled MSCs exosomes were analyzed by NanoSight™ (0.5 ml), flow cytometry (1 ml) and tested for endotoxin (using 0.5 ml of pooled samples) and sterility (using 1 ml of pooled samples, as detailed above). The exosomes (69 ml final volume) were finally aliquoted in a cryoglass vials, each containing (2 ml), and stored at −80° C. For the manufacture of future clinical product, the exosomes will be directly processed for large scale electroporation (see below for details), then aliquoted and stored at −80° C.

Measurement of particle size and concentration distribution with NTA: Isolated exosome suspensions were analyzed using the NanoSight™ LM 10 instrument (NanoSight Ltd). The analysis settings were optimized and kept constant between samples, and each video was analyzed to give the mean, mode, median and estimated concentration for each particle size.

Quantification of exosomes by microBCA assay: MSC exosomes resuspended in CB were washed with 1×PBS and ultra-centrifuged at 100,000 g for 3 h in a type SW 41 Ti totor (Beckman Coulter). The washed MSCs exosomes were then measured again by NanoSight™ and analyzed for total protein content using the microBCA Protein Assay Reagent Kit (Thermo Scientific) following the manufacturer's specifications.

Electroporation of exosomes: $0.5 \times 10^{12}$ total number of MSCs-derived exosomes and 0.5 mg of siRNA source 2 (Avecia) were mixed in 20 ml of clinical buffer. These exosomes were electroporated using the 4D Nucleofator LV unit (Lonza), in a closed system. The LV Nucleocuvette™ Cartridge is a new cuvette system that allows electroporation up to 20 ml. The Cartridge is connected to two reservoir bags (inlet and outlet), and a peristaltic pump that fills the cartridge with 1 ml per time. The outlet bag is maintained on ice during all the procedure and the procedure takes approximately 10 min to be completed. Post electroporation, the exosomes were analyzed by NanoSight™, tested for endotoxin and sterility (as detailed above), aliquoted in a cryovial, and stored at −80° C. These exosomes were then thawed on ice, and used for subsequent in vitro and in vivo experiments. For in vitro experiments, the exosomes were diluted for downstream applications at detailed below. For in vivo experiments, 109 electroporated exosomes were diluted in 100 µL of research buffer or clinical buffer.

Electron Microscopy: Fixed specimens at an optimal concentration were placed onto a 300 mesh carbon/formvar coated grids and allowed to absorb to the formvar for a minimum of 1 min Grids were rinsed with PBS and were placed in 2.5% Glutaraldehyde in 0.1M phosphate buffer for 15 min After rinsing in PBS and distilled water the grids were allowed to dry and stained for contrast using uranyl acetate. The samples were viewed with a Tecnai Bio Twin transmission electron microscope (FEI, Hillsboro, Oreg.) and images were taken with an AMT CCD Camera (Advanced Microscopy Techniques, Danvers, Mass.).

Flow cytometry analyses of exosomes: Exosomes from MSCs were isolated as described above and resuspended in 200 µl of PBS. Aldehyde/sulfate beads (10 Life Technologies) were added to the solution and beads and exosomes mixture allowed to mix using a benchtop rotator for 15 minutes at room temperature. PBS (600 µl) was then added to the solution and mixing was continued overnight at 4° C. 1 M Glycine (400 µl) was added and mixing was continued for 1 h at room temperature. The mixture was then spin down at 8,000 g for 1 min. The precipitate was then resuspended in 100 µL of 10% BSA in PBS, and mixed for 45 min at room temperature. The mixture was spun down at 8,000 g for 1 min and the supernatant aspirated. The beads with the exosomes attached (pellet) were then resuspended in 20 µl of 2% BSA in PBS and immunolabeled for CD47, CD63, CD81, CD9, CD29, CD90 or an isotype control. The exosomes bound to beads were incubated with 1 µl of anti-CD47 antibody (eBiosciences, catalog no. 14-0479) or 1 µl of anti-CD63 (BD biosciences, catalog no. 556019), or 1 µl of anti CD-81 antibody (BD Biosciences, catalog no. 555675), or 1 µl of anti-CD9 antibody (Sigma, catalog no. SAB4700092), or 1 µl of anti-CD29 antibody (Biolegend, catalog no. 303001), or 1 µl of anti-CD90 antibody a (Biolegend, catalog no. 328101), or 1 µl of Mouse IgG1, κ isotype control antibody (BD Biosciences, catalog no. 555746) in 20 µl volume, and mixed at room temperature for 30 min. The mixture was then centrifuged at 8,000 g for 1 min, the supernatant aspirated, and the pellet resuspended in 20 µl of 2% BSA in PBS. Then, 1 µl of secondary antibody (Invitrogen, catalog no. A21202) was added to the samples and isotype control. All samples were then mixed at room temperature for 1 h. The samples were then centrifuged at 8,000 g for 1 min, the supernatant aspirated, and pellet resuspended in 200 µl of 2% BSA in PBS. The exosomes bound to the beads were washed three times with 2% BSA in PBS. The expression of exosomes markers (CD9, CD63 and CD81, CD47, and mesenchymal markers (CD29 and CD90) was analyzed using the LSR Fortessa X-20 cell analyzer. Data were analyzed using FlowJoR software (TreeStar Inc.). The flow cytometry data was acquired side by side for both isotype control and samples for each experiment. The flow cytometry experiment was repeated 2 independent times using the same exosomes preparation.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

International Patent Publication No. WO 00/37504
International Patent Publication No. WO 01/14424
International Patent Publication No. WO 98/42752
International Patent Publication No. WO1995001994
International Patent Publication No. WO1998042752
International Patent Publication No. WO2000037504
International Patent Publication No. WO2001014424
International Patent Publication No. WO2006/121168
International Patent Publication No. WO2009/101611
International Patent Publication No. WO2009/114335
International Patent Publication No. WO2010/027827
International Patent Publication No. WO2011/066342
International Patent Publication No. WO2015016718
U.S. Pat. No. 4,870,287
U.S. Pat. No. 5,760,395
U.S. Pat. No. 5,844,905
U.S. Pat. No. 5,885,796
U.S. Pat. No. 8,008,449
U.S. Pat. No. 8,017,114
U.S. Pat. No. 8,119,129
U.S. Pat. No. 8,329,867
U.S. Pat. No. 8,354,509
U.S. Pat. No. 8,735,553
U.S. Patent Publication No. 20110008369
U.S. Patent Publication No. 2014022021
U.S. Patent Publication No. 20140294898

What is claimed is:

1. A method of manufacturing exosomes from mesenchymal stem cells (MSCs) comprising:
    (a) culturing the MSCs in a functionally closed bioreactor to 75-95% confluency in media comprising human platelet lysate (PLT);
    (b) further culturing the cells in media essentially free of PLT;
    (c) collecting one or more conditioned media fractions from the bioreactor wherein conditioned media fractions are collected every 24-48 hours; and (d) isolating exosomes from the conditioned media fractions.

2. The method of claim 1, wherein each conditioned media fraction is stored at −80° C. after collection.

3. The method of claim 2, wherein the conditioned media fractions are thawed and pooled prior to step (d).

4. The method of claim 1, wherein the MSCs are further defined as bone marrow-derived MSCs or adipose-derived MSCs.

5. The method of claim 1, wherein the MSCs are further defined as adipose-derived MSCs.

6. The method of claim 1, further comprising seeding the bioreactor with at least $1 \times 10^7$ MSCs prior to step (a).

7. The method of claim 6, wherein the MSCs are seeded at a density of about 400-500 cells/cm$^2$.

8. The method of claim 1, wherein the closed bioreactor is a hollow fiber bioreactor.

9. The method of claim 1, wherein the PLT is at a concentration of 5% in the media of step (a).

10. The method of claim 1, wherein fresh media is added continuously to the MSCs in the bioreactor.

11. The method of claim 1, wherein the cells are cultured at 5% oxygen.

12. The method of claim 1, wherein culturing of step (a) is for 5-10 days.

13. The method of claim 12, wherein culturing of step (a) is for 8 days.

14. The method of claim 1, wherein the MSCs are cultured to 80-90% confluency.

15. The method of claim 1, wherein culturing of step (b) is for 24-72 hours.

16. The method of claim 1, wherein the media of step (b) is free of PLT.

17. The method of claim 1, wherein the MSCs are washed between step (a) and (b).

18. The method of claim 1, wherein the MSCs are cultured in serum-free, defined media.

19. The method of claim 1, wherein steps (a)-(d) are performed under serum-free conditions.

20. The method of claim 1, wherein the conditioned media fractions are collected in sealed bags.

21. The method of claim 1, wherein the conditioned media fractions are each 200-300 mL in volume.

22. The method of claim 1, wherein the conditioned media fractions are collected for 10-14 days.

23. The method of claim 1, wherein at least 5 conditioned media fractions are collected.

24. The method of claim 1, wherein steps (a)-(d) are performed in less than 3 weeks.

25. The method of claim 1, wherein each conditioned media fraction comprises $9 \times 10^{11}$ to $50 \times 10^{11}$ exosomes.

26. The method of claim 1, wherein at least $10 \times 10^{12}$ exosomes are isolated in step (c).

27. The method of claim 1, wherein isolating comprises filtration and ultracentrifugation of the pooled fractions to obtain an exosome-containing pellet and resuspending the exosome-containing pellet in a buffer.

28. The method of claim 27, wherein isolating is performed in a functionally-closed manner using a pump and heat-sealed tubing.

29. The method of claim 27, wherein filtration is further defined as passing the pooled fractions through a 0.2 µm filter.

30. The method of claim 27, wherein isolating further comprises a centrifugation step prior to filtration to remove large cell debris.

31. The method of claim 1, further comprising loading the exosomes with a therapeutic agent.

32. The method of claim 31, wherein the therapeutic agent comprises one or more cytokines, chemotherapeutic drugs, nucleic acids, small molecules, or proteins.

33. The method of claim 32, wherein the nucleic acids comprise DNA and/or RNA.

34. The method of claim 33, wherein the RNA is siRNA, miRNA, or shRNA.

35. The method of claim 31, wherein loading comprises electroporating the exosomes.

36. The method of claim 35, wherein the method does not comprise washing the exosomes or exchanging buffers between step (d) and electroporating.

37. The method of claim 36, wherein the number of exosomes from step (d) to the number of loaded exosomes does not decrease by more than 20%.

* * * * *